United States Patent
Hilfiker-Kleiner et al.

(10) Patent No.: US 10,775,389 B2
(45) Date of Patent: Sep. 15, 2020

(54) METHOD FOR DETECTING PLASMINOGEN ACTIVATOR INHIBITOR-1 IN A SAMPLE

(71) Applicant: Medizinische Hochschule Hannover, Hannover (DE)

(72) Inventors: Denise Hilfiker-Kleiner, Hannover (DE); Justus Nonhoff, Hannover (DE)

(73) Assignee: Medizinische Hochschule Hannover, Hannover (DE)

( * ) Notice: Subject to any disclaimer, the term of this patent is extended or adjusted under 35 U.S.C. 154(b) by 0 days.

(21) Appl. No.: 15/758,293

(22) PCT Filed: Sep. 8, 2016

(86) PCT No.: PCT/EP2016/071188
§ 371 (c)(1),
(2) Date: Mar. 7, 2018

(87) PCT Pub. No.: WO2017/042278
PCT Pub. Date: Mar. 16, 2017

(65) Prior Publication Data
US 2018/0246124 A1    Aug. 30, 2018

(30) Foreign Application Priority Data
Sep. 9, 2015 (EP) .................... 15184498

(51) Int. Cl.
*G01N 33/68* (2006.01)
*C12Q 1/6883* (2018.01)

(52) U.S. Cl.
CPC ....... *G01N 33/6893* (2013.01); *C12Q 1/6883* (2013.01); *G01N 33/689* (2013.01); *G01N 33/6887* (2013.01); *C12Q 2600/106* (2013.01); *C12Q 2600/118* (2013.01); *C12Q 2600/156* (2013.01); *C12Q 2600/158* (2013.01); *G01N 2800/325* (2013.01); *G01N 2800/50* (2013.01)

(58) Field of Classification Search
CPC ............. G01N 33/6887; G01N 33/689; G01N 33/6893; G01N 2800/325; G01N 2800/50; C12Q 1/6883; C12Q 2600/106; C12Q 2600/118; C12Q 2600/156; C12Q 2600/158
See application file for complete search history.

(56) References Cited

FOREIGN PATENT DOCUMENTS

| FR | 3017955 A1 | 8/2015 |
|---|---|---|
| WO | 2010019234 A1 | 2/2010 |

OTHER PUBLICATIONS

Gerhardt (J Thrombosis and Haemostasis, 2005, 3, 686-91).*
Bajou et al., "PAI-1 Mediates the Antiangiogenic and Profibrinolytic Effects of 16K Prolactin", Nature Medicine, vol. 20, No. 7, pp. 741-747, (2014).
Bello et al., "Molecular Mechanisms of Peripartum Cardiomyopathy: A Vascular/Hormonal Hypothesis", Trends in Cardiovascular Medicine, vol. 25, No. 6, pp. 499-504, (2015).
Elokdah et al., "Tiplaxtinin, a Novel, Orally Efficacious Inhibitor of Plasminogen Activator Inhibitor-I: Design, Synthesis, and Preclinical Characterization", Journal of Medicinal Chemistry, vol. 47, No. 14, pp. pp. 3491-3494, (2004).
European Search Report dated Dec. 3, 2015, received in EP 15 18 4498.
Halkein et al., "MicroRNA-146a is a Therapeutic Target and Biomarker for Peripartum Cardiomyopathy", Journal of Clinical Investigation, vol. 123, No. 5, pp. 2143-2154, (2013).
International Search Report dated Nov. 22, 2016 and received in PCT/EP2016/071188.

* cited by examiner

*Primary Examiner* — Robert S Landsman
(74) *Attorney, Agent, or Firm* — Michele M. Wales; Inhouse Patent Counsel, LLC

(57) ABSTRACT

The present invention relates to a method for identifying a subject, which has peripartum cardiomyopathy (PPCM) or which has a risk for developing PPCM, wherein the method comprises analyzing the amount and/or activity of plasminogen activator inhibitor-1 (PAI-1); and/or the genotype of the PAI-1 gene. The invention also relates to an inhibitor of PAI-1 for use in the treatment of PPCM. Also a method of treating PPCM in a subject in need of such a treatment, wherein said method comprises administering to said subject an effective amount of an inhibitor of PAI-1 is comprised in the present invention. Moreover, the present invention further relates to the use of a binding molecule for identifying a subject, which has PPCM or which has a risk for developing PPCM, wherein said binding molecule specifically binds to PAI-1.

Figure 1:
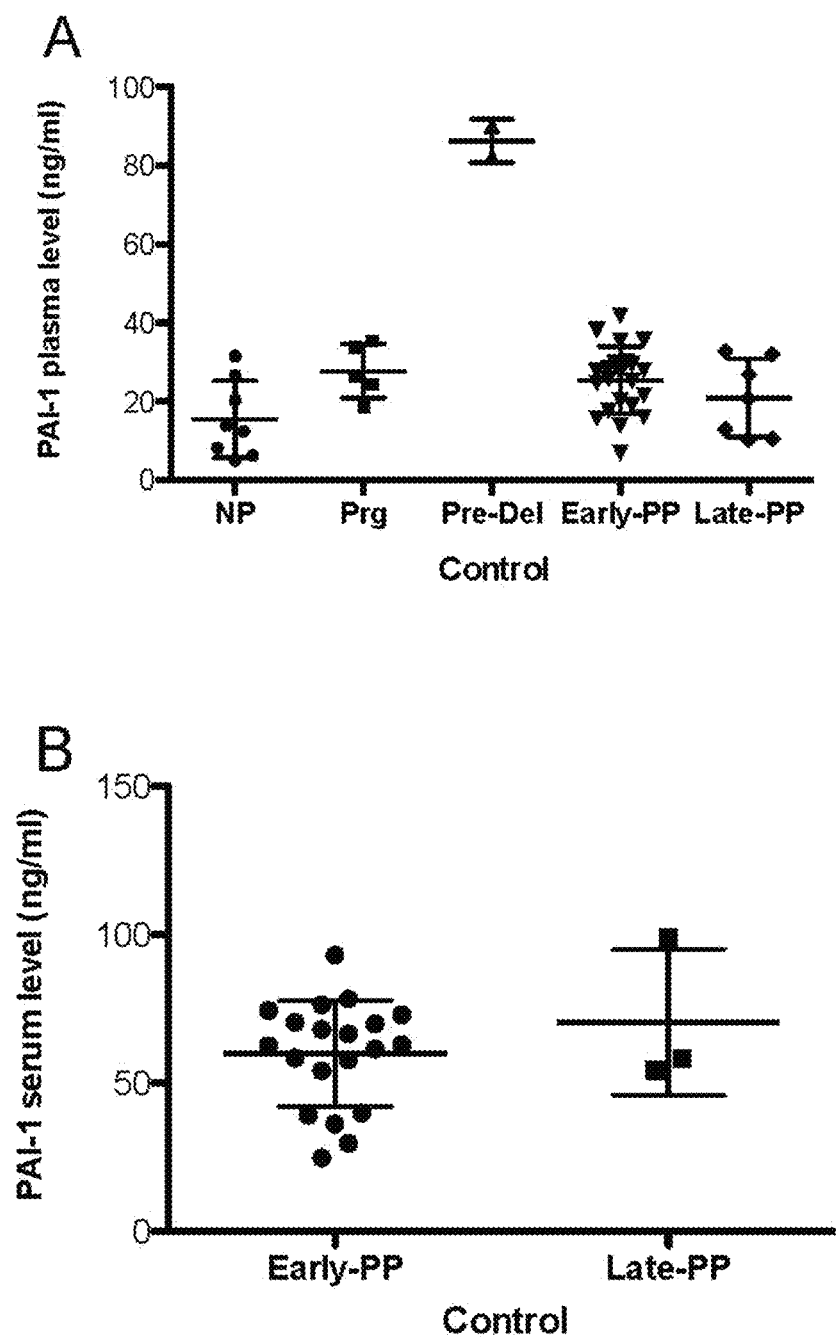
Figure 1:
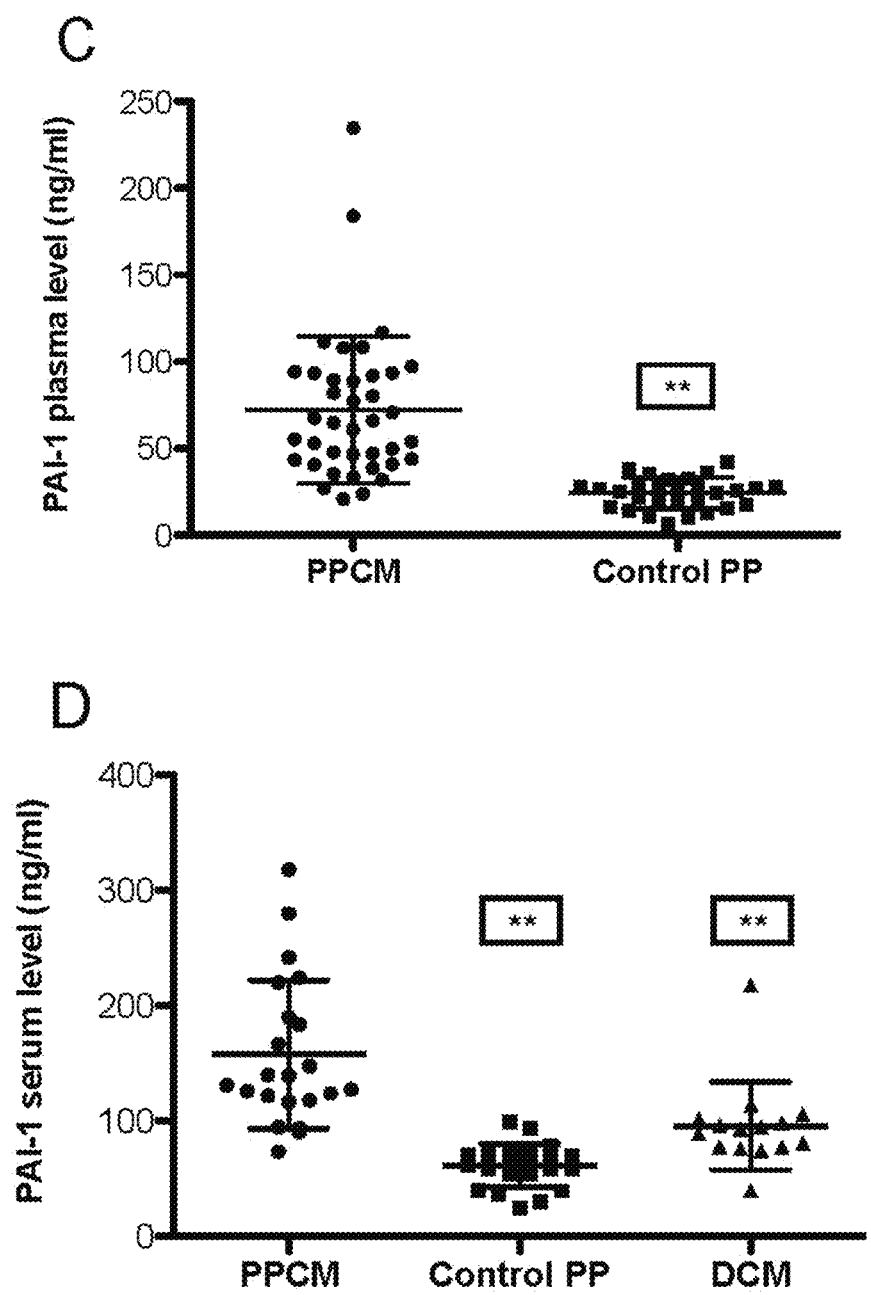

16 Claims, 9 Drawing Sheets
Specification includes a Sequence Listing.

Figure 4 cont.

C

```
                                        -747
PAI-1 promoter    CCAGCACACCTCCAACCTCAGCCAGACAAGGTTGTTGACACAAGAGAGCCC
01-016 clone #1   CCAGCACACCTCCAACCTCAGCCAGACAAGGTTGTTGACACAAGAGAGCCC
01-016 clone #2   CCAGCACACCTCCAACCTCAGCCAGACAAGGTTGTTGACACAAGAGAGCCC
01-016 clone #3   CCAGCACACCTCCAACCTCAGCCAGACAAGGTTGTTGACACAAGAGAGCCC
01-016 clone #4   CCAGCACACCTCCAACCTCAGCCAGACAAGGTTGTTGACACAAGAGAGCCC
01-016 clone #5   CCAGCACACCTCCAACCTCAGCCAGACAAGGTTGTTGACACAAGAGAGCCC -675
PAI-1 promoter    TCAGGGGCACAGAGAGAGTCTGGACACGTGGGGAGTCAGCCGTGTATCATC
01-016 clone #1   TCAGGGGCACAGAGAGAGTCTGGACACGTGGGGAGTCAGCCGTGTATCATC
01-016 clone #2   TCAGGGGCACAGAGAGAGTCTGGACACGTGGGGAGTCAGCCGTGTATCATC
01-016 clone #3   TCAGGGGCACAGAGAGAGTCTGGACACGTGGGGAGTCAGCCGTGTATCATC
01-016 clone #4   TCAGGGGCACAGAGAGAGTCTGGACACGTGGGGAGTCAGCCGTGTATCATC
01-016 clone #5   TCAGGGGCACAGAGAGAGTCTGGACACGTGGGGAGTCAGCCGTGTATCATC
```

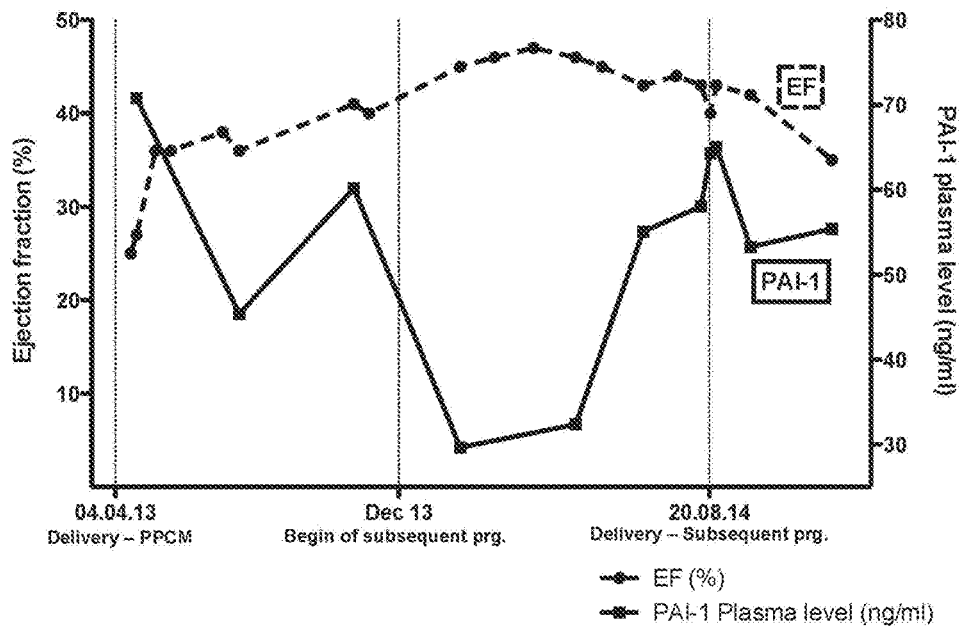

D  PAI-1 + EF of a PPCM patient during and after subsequent prg.

A

PAI-039

B

Bromocriptine

METHOD FOR DETECTING PLASMINOGEN ACTIVATOR INHIBITOR-1 IN A SAMPLE

CROSS-REFERENCE TO RELATED APPLICATIONS

This application is a § 371 National Stage Application of PCT/EP2016/071188 filed on Sep. 8, 2016 which claims priority to EP 15184498.2 filed on Sep. 9, 2015. These documents are hereby incorporated by reference in their entirety.

The present invention relates to a method for identifying a subject, which has peripartum cardiomyopathy (PPCM) or which has a risk for developing PPCM, wherein the method comprises analyzing the amount and/or activity of the plasminogen activator inhibitor-1 (PAI-1); and/or the genotype of the PAI-1 gene. The invention also relates to an inhibitor of PAI-1 for use in the treatment of PPCM. Also a method of treating PPCM in a subject in need of such a treatment, wherein said method comprises administering to said subject an effective amount of an inhibitor of PAI-1 is comprised in the present invention. Moreover, the present invention further relates to the use of a binding molecule for identifying a subject, which has PPCM or which has a risk for developing PPCM, wherein said binding molecule specifically binds to PAI-1.

Peripartum cardiomyopathy (PPCM, sometimes also referred to as postpartum cardiomyopathy) is an idiopathic, life-threatening heart disease characterized by a sudden onset of heart failure in the last month of pregnancy and/or in the first months postpartum in previously heart-healthy women (Hilfiker-Kleiner, 2014, Nat Rev Cardiol. 11(6):364-70). The Working Group on PPCM from the Heart Failure Association of the ESC suggested the following definition of PPCM: "Peripartum cardiomyopathy is an idiopathic cardiomyopathy presenting with heart failure secondary to left ventricular systolic dysfunction towards the end of pregnancy or in the months following delivery, where no other cause of heart failure is found. It is a diagnosis of exclusion. The left ventricle may not be dilated but the ejection fraction is nearly always reduced below 45%" (Sliwa, 2010, Eur J Heart Fail. 12(8):767-78).

The actual triggers that initiate the pathophysiology of PPCM are still unknown, but it has been recently proposed that cardiac angiogenic imbalances resulting from the complex pregnancy-related immune system and hormonal changes play a role (Patten I S, 2012, Nature. 485(7398):333-8; Fett, 2014, World J Cardiol. 6(3):87-99). It has been suggested that oxidative stress and the production of the angiostatic and proapoptotic 16 kDa prolactin fragment (16K prolactin) plays a role in PPCM (Hilfiker-Kleiner, 2007, Cell. 128: 589-600; Hilfiker-Kleiner, 2014, Nat Rev Cardiol. 11(6):364-70; Patten, 2012, Nature. 485(7398):333-8; Hilfiker-Kleiner, 2014, Nat Rev Cardiol. 11(6):364-70; Sliwa, 2010, Eur J Heart Fail. 12(8):767-78). Other studies postulate that the final proof for the cardiotoxicity of the 16K prolactin still lacks (Fett, 2014, World J Cardiol. 6(3):87-99). However, it has been described that an elevated 16K prolactin level induces the expression of the microRNA-146a (miR-146a), which mediates the downstream attenuation of angiogenesis (Halkein, 2013, J Clin Invest. 123(5):2143-54).

However, the cause of PPCM is still unknown, as it suddenly occurs in women, which seem to have a healthy heart. The PPCM diagnosis currently relies on a high index of suspicion. In addition, diagnosing PPCM is difficult and often long lasting, because PPCM symptoms such as dyspnoea, exercise intolerance, cough, and orthopnoeas are often hardly distinguishable from peripartum-associated physiological discomfort (Hilfiker-Kleiner, 2008, Deutsches Ärzteblatt, Jg. 105, Heft 44). Moreover, postpartal women are usually not examined by experienced cardiologists but by gynecologists or family doctors. This further delays the diagnosis of PPCM. However, early PPCM diagnosis significantly improves the patient's chance of full recovery, whereas delayed PPCM diagnosis frequently results in an increased rate of major adverse events such as death or life-threatening complications (Fett, 2014, World J Cardiol. 6(3):87-99). Moreover, at present it is impossible to distinguish between a PPCM and a not diagnosed mild preexisting cardiomyopathy that was accelerated by the pregnancy stress in a peripartum woman. However, this distinction is of high importance as non-peripartum cardiomyopathies have a lower chance for recovery and may need invasive therapies such as implantable cardioverter defibrillator (ICD), cardiac resynchronization therapy (CRT), assist device and/or heart transplantation. In contrast, women with PPCM frequently recover from disease and risk phases and can be prophylactically protected from disease symptoms with non-invasive methods such as lifevest wearable defibrillator. In fact, they do usually not need such invasive treatment and therefore, these therapies unnecessarily harm these (usually young) women with lifelong impact. Moreover, these invasive treatments may unnecessarily render good quality childcare impossible. Therefore, it is highly important to find means and methods, which allow a fast, specific and valuable diagnosis of PPCM. Up to now no specific biomarkers for PPCM exist. General markers for cardiomyopathy are usually within the normal range in women with PPCM. Moreover, inflammation and stress factors are often upregulated postpartum and are therefore also not useful for diagnosing PPCM. Also the factors, which are known to change their amount or activity during complications in pregnancy (e.g. sFlt1, PLGF, or Relaxin), appear not useful as PPCM markers, as these factors have highly specific kinetics during normal pregnancy. Therefore, it is hard to define any thresholds, which indicate that complications (such as PPCM) may occur.

Current standard treatments of PPCM are mainly evidence-based and usually follow the European Society of Cardiology Guidelines for heart failure (Sliwa, 2010, Eur J Heart Fail. 12(8):767-78; Dickstein, 2008, Eur J Heart Fail. 10(10):933-989). For instance, the therapy can involve a combination of tolerable dosages of diuretics, angiotensin converting enzyme (ACE) inhibitors and beta-blockers. However, combining these drugs with further medicaments would have the advantage that the doses of the individual medicaments can be reduced without a significant loss of therapeutic activity. Using a lower dose of these medicaments has the advantage that it is easier to not exceed the maximum tolerated dose (i.e. the highest dose of the medicament that will produce the desired effect without unacceptable toxicity). Therefore, new therapeutic agents for use in the treatment of PPCM are highly desirable.

Accordingly, there is a high need to identify biomarkers that allow for robust PPCM diagnosis, preferably already in an early disease stage. In addition, as stated above, there is also a high need for a new PPCM medication. Thus, the technical problem underlying the present invention is the provision of new means and methods for the diagnosis and treatment PPCM.

The technical problem is solved by the provision of the embodiments as characterized in the claims.

Accordingly, the present invention relates to a method for identifying a subject, which has PPCM or which has a risk for developing PPCM, wherein the method comprises:
 (a) analyzing in a sample obtained from a test subject
   (a1) the amount of PAI-1 and/or the activity of PAI-1 (e.g. of the PAI-1/16K prolactin/uPAR-NF-kB signaling); and/or
   (a2) the genotype of the PAI-1 gene;
 (b) comparing
   (b1) said amount and/or activity with reference data corresponding to the amount and/or activity of PAI-1 of at least one reference subject; and/or
   (b2) said genotype of the PAI-1 gene with reference data corresponding to the genotype of the PAI-1 gene of at least one reference subject; and
 (c) identifying a subject, which has PPCM or which has a risk for developing PPCM based on the comparison step (b).

Accordingly, the present invention relates to a method for identifying a subject, which has peripartum cardiomyopathy or which has a risk for developing peripartum cardiomyopathy, wherein the method comprises:
 (a) analyzing in a sample
   (a1) the amount and/or activity of plasminogen activator inhibitor-1; and/or
   (a2) the genotype of the plasminogen activator inhibitor-1 gene;
 (b) comparing
   (b1) said amount and/or activity with reference data corresponding to the amount and/or activity of plasminogen activator inhibitor-1 of at least one reference subject; and/or
   (b2) said genotype of the plasminogen activator inhibitor-1 gene with reference data corresponding to the genotype of the plasminogen activator inhibitor-1 gene of at least one reference subject; and
 (c) identifying a subject, which has peripartum cardiomyopathy or which has a risk for developing peripartum cardiomyopathy based on the comparison step (b).

In this method the sample is obtained from a test subject, particularly a patient, more particularly a human patient and/or a human subject.

Accordingly, the present invention also provides for a method for diagnosing peripartum cardiomyopathy or the risk for developing peripartum cardiomyopathy, wherein the method comprises:
 (a) analyzing in a sample obtained from a test subject
   (a1) the amount and/or activity of plasminogen activator inhibitor-1; and/or
   (a2) the genotype of the plasminogen activator inhibitor-1 gene;
 (b) comparing
   (b1) said amount and/or activity with reference data corresponding to the amount and/or activity of plasminogen activator inhibitor-1 of at least one reference subject; and/or
   (b2) said genotype of the plasminogen activator inhibitor-1 gene with reference data corresponding to the genotype of the plasminogen activator inhibitor-1 gene of at least one reference subject; and
 (c) diagnosing peripartum cardiomyopathy or a risk for developing peripartum cardiomyopathy based on the comparison step (b).

Said peripartum cardiomyopathy is diagnosed in a human subject and/or a human patient.

The present invention solves the above identified technical problem since, as documented herein below and in the appended Examples, it was surprisingly found that the level and activity of PAI-1 is considerably increased specifically in women with PPCM. Therefore, the present invention advantageously provides a method for identifying a subject (preferably a human woman), which has PPCM or which has a risk for developing PPCM. Or, in other words, the present invention advantageously provides a method for the diagnosis of PPCM or for diagnosing the risk for developing PPCM.

As described above the prior art fails to provide a method for specifically diagnosing PPCM, in particular for distinguishing a PPCM from a non-peripartum cardiomyopathy (e.g. a mild preexisting cardiomyopathy that was accelerated by the pregnancy stress). Therefore, in the prior art PPCM women are frequently diagnosed late and/or treated with therapies for patients with non-peripartum cardiomyopathies. These may cause progression of the disease with permanent cardiac damage to an irreversible state needing invasive therapies such as ICD, CRT, assist device and/or heart transplantation. Moreover, unspecific diagnosis for severe heart failure may lead to premature invasive therapies, which unnecessarily harm the (usually young) PPCM women who would have had the potential to recover.

Figure 2:
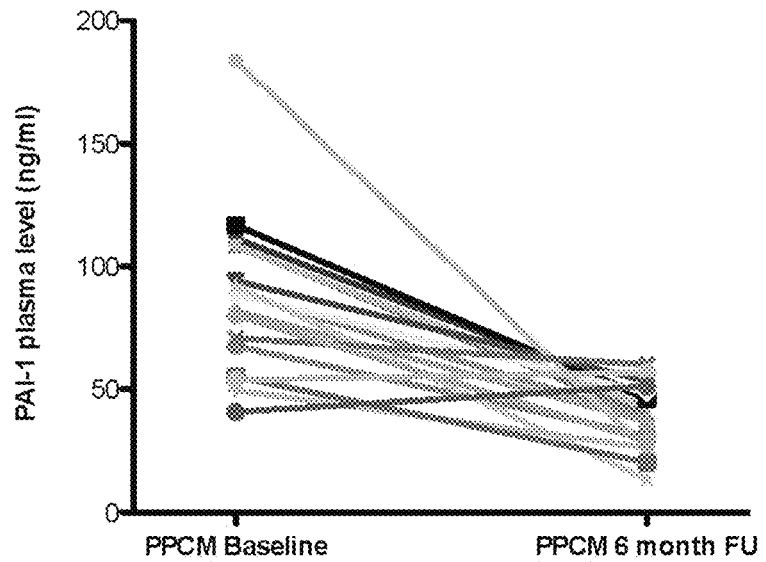
Figure 2:
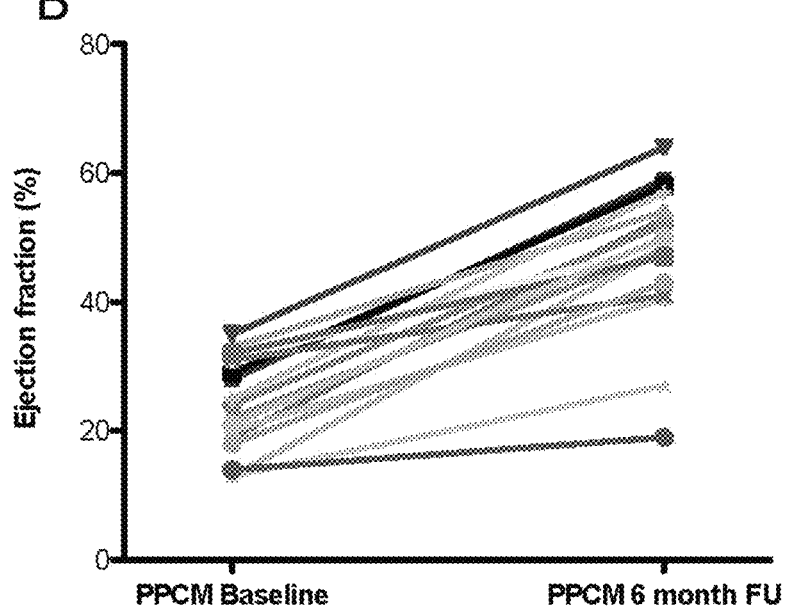
Figure 2:
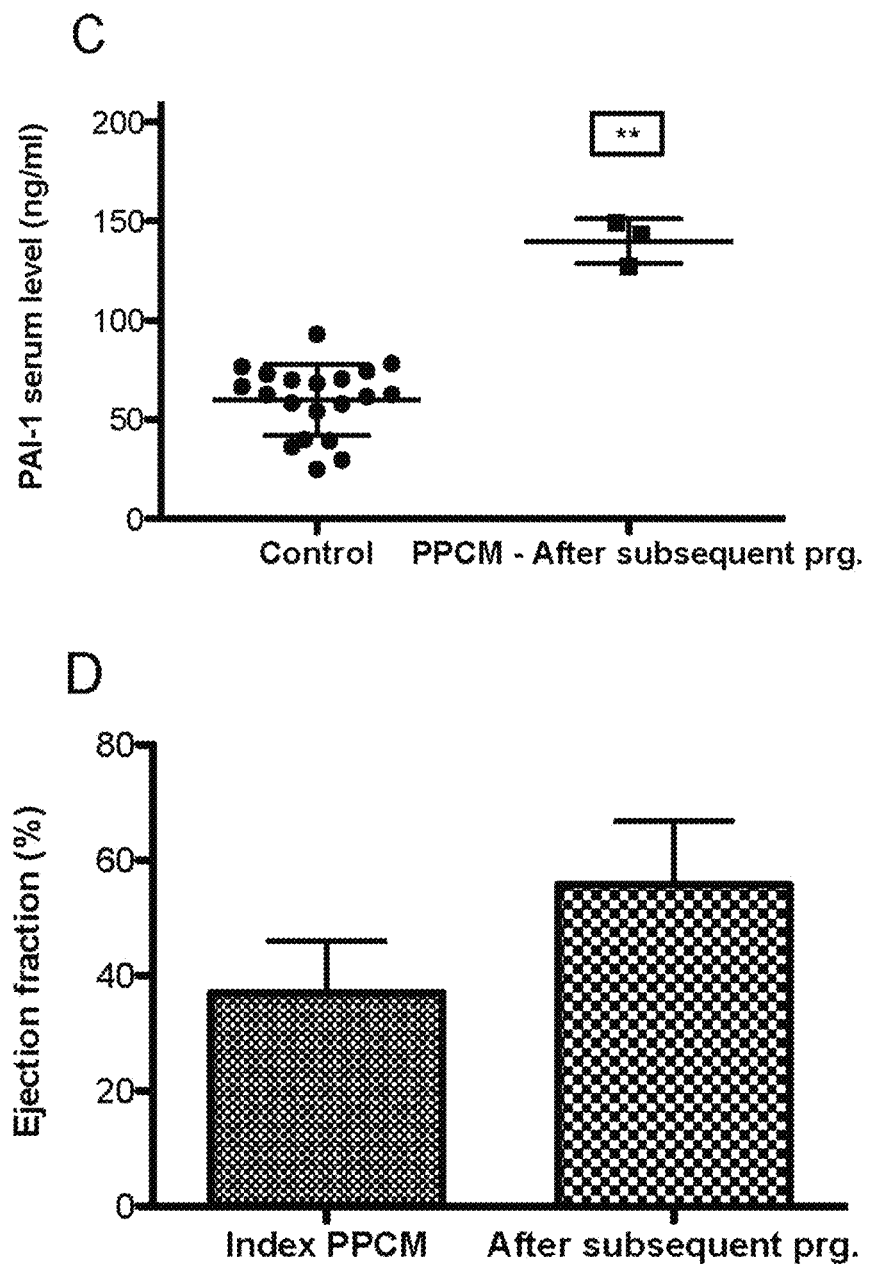
Figure 3:
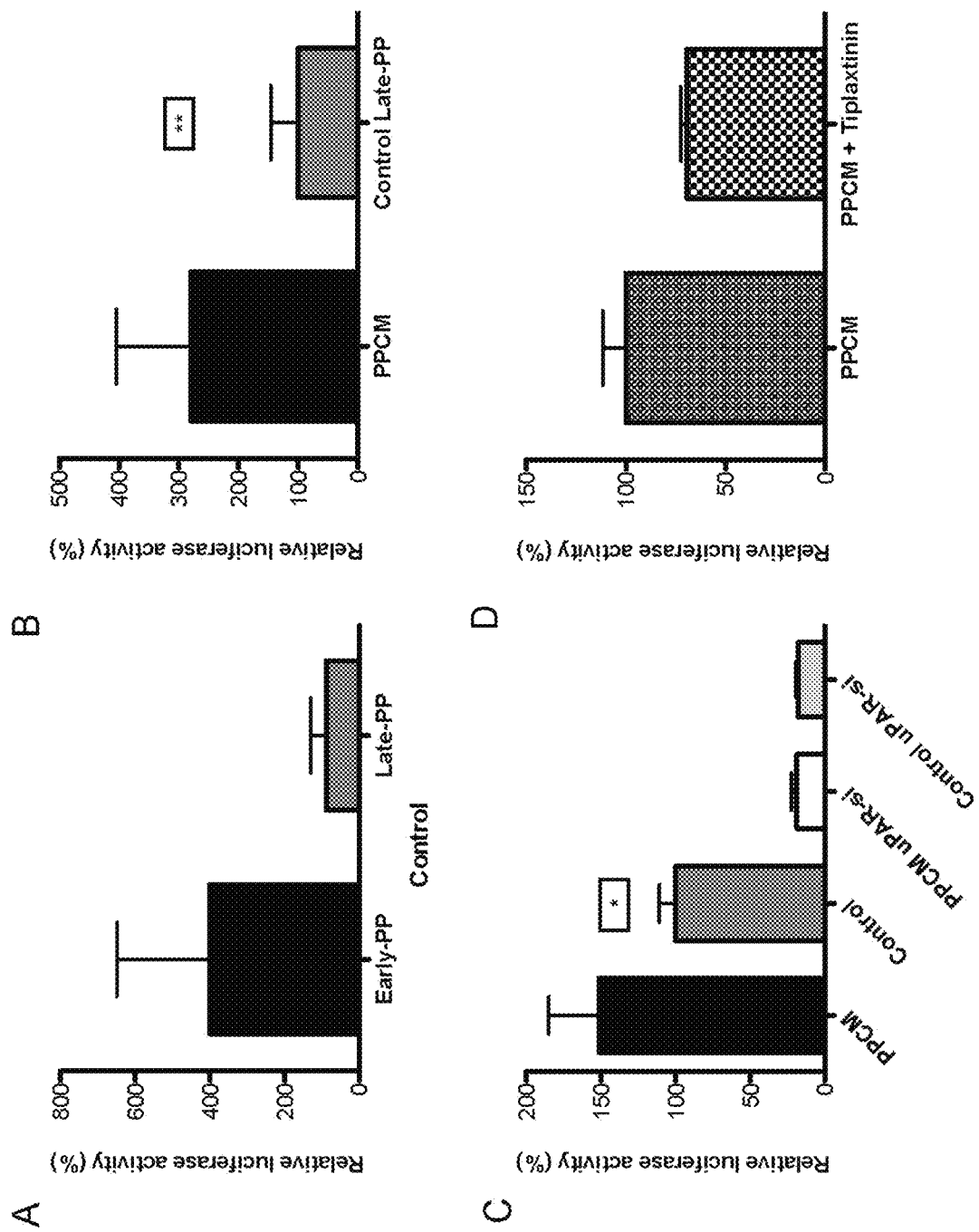

In context of the present invention it has surprisingly been found that the PAI-1 level and/or activity indicate the presence or the predisposition to PPCM (see, e.g. FIGS. 1-3). PAI-1 (sometimes also referred to as serpin E1) is an endogenous inhibitor of tissue-type plasminogen activator (tPA) and urokinase-type plasminogen activator (uPA), the activators of plasminogen and hence fibrinolysis. In the prior art, elevated levels of PAI-1 have been proposed to be marker for fibrinolytic and age-related disease progression (Ghosh, 2012, J Cell Physiol. 227(2):493-507).

In addition, altered PAI-1 levels have been linked to cardiovascular pathology (Alessi, 2004, Arch Mal Coeur Vaiss. 97(6):673-8). In particular, high plasma levels of PAI-1 worsen the prognosis of myocardial infarction in the acute phase and are considered to be a risk factor for coronary heart disease, as well as for cardiovascular diseases (Alessi, 2004, Arch Mal Coeur Vaiss. 97(6):673-8; Gils, 2004, Thromb Haemost. 91(3):425-37). In WO 2008/080030 A2 PAI-1 has been described as one of several indicators of cardiac pathology. However, not only elevated PAI-1 levels but also PAI-1 deficiency has been linked to cardiac pathology, as both induce cardiac-selective fibrosis (Ghosh, 2012, J Cell Physiol. 227(2):493-507). Therefore, the prior art does not describe PAI-1 to be a valuable marker for cardiac diseases. Furthermore, the fact that PAI-1 has been linked to cardiovascular pathology does in no way indicate that PAI-1 plays also a role in PPCM, as it is known in the art that markers of non-peripartum (e.g. preexisting) cardiomyopathy such as troponin T are in the normal range in PPCM women (Haghikia, 2013, Basic Res Cardiol. 108(4):366). In contrast, the appended Examples demonstrate that women with genetic cases of cardiomyopathy (i.e. who do not have PPCM) did not show elevated PAI-1 levels (see, e.g. FIG. 1). Thus, the herein provided diagnostic method may be used for distinguishing PPCM from other forms of heart failure (such as dilated cardiomyophathy).

PAI-1 has been linked to preeclampsia (PE), which is a disorder of pregnancy characterized by high blood pressure and a large amount of protein in the urine (WO 2014/142752 A1). However, although PE has been described as a risk factor for the development of PPCM (Bello, 2014, J Am Coll Cardiol. 62(18):1715-23), PE is an independent disease that is neither necessary nor sufficient to cause PPCM. In particular, more than 50% of the women with PPCM have no history of pregnancy associated hypertensive disorders and/or PE and, conversely, more than 90% of women with PE do not develop PPCM (Bello N, 2014, J Am Coll Cardiol. 62(18):1715-23; Haghikia, 2013, Basic Res Cardiol. 108(4):366). Therefore, markers for PE are not considered to be specific and valuable PPCM markers. Quite to the contrary, PE markers are thought to be not useful for diagnosing PPCM, because they are thought to produce a high rate of false positive and false negative results.

16K prolactin was found to be an interaction partner of PAI-1 in tumor cells (Bajou, 2014, Nat Med. 20(7):741-7). However, the function of 16K prolactin in tumor cells is completely unrelated to its role in PPCM pathophysiology. For example, in tumor cells 16K prolactin and PAI-1 are beneficial for the patient, i.e. mediate anti-tumorigenic effects (Bajou, 2014, Nat Med. 20(7):741-7). Accordingly, this study teaches that PAI-1 may play a role in tumor growth, but not at all indicates that PAI-1 is involved in PPCM.

However, contrary to the teaching of the prior art, in context of the present invention it has been surprisingly found that (in addition to miR-146a) also the level of PAI-1 is increased in women with PPCM. In addition, the appended Examples show that also the activity of PAI-1 is considerably increased in newly diagnosed PPCM women (see, e.g. FIG. 3). Thus, in context of the present invention it has unexpectedly been found that PAI-1 represents a valuable marker of PPCM, which advantageously simplifies and accelerates the diagnosis of PPCM.

The herein provided "method for identifying a subject, which has PPCM or which has a risk for developing PPCM" is advantageously useful for diagnosing PPCM. Therefore, herein the "method for identifying a subject, which has PPCM or which has a risk for developing PPCM" of the invention, is also designated as "diagnostic method" of the invention. Herein, "diagnosis" or "diagnosing" means identifying an existing PPCM as well as identifying a risk for developing PPCM. Preferably, the herein provided diagnostic method is a method for diagnosing an existing PPCM (i.e. for identifying a subject, which has PPCM). However, the herein provided diagnostic method is also useful for predicting (i.e. assessing) whether a subject (preferably a human woman) will develop PPCM. Thus, the herein provided diagnostic method can also be used for identifying a subject (preferably a human woman), which has a risk for developing PPCM. For example, the subject can be identified as having a risk for developing PPCM in the first months after delivery. This is specifically important for women who had a PPCM in a previous pregnancy and may develop a relapse for the disease. In fact the appended Examples show that most PPCM patients diagnosed after delivery display increased PAI-1 serum and plasma levels compared to reference control subjects analyzed after delivery that had no PPCM (see, e.g. FIG. 1). The PAI-1 levels in PPCM decrease under heart failure medication as determined during follow up measurements, which correlates with improvement of the condition (see, e.g. FIG. 2). In addition, the appended Examples further demonstrate that PPCM patients with a subsequent pregnancy who have a high risk for relapse display higher plasma and serum PAI-1 levels in the first week after delivery compared to healthy controls in the first week postpartum, implying that PAI-1 could have a predictive value for PPCM even before onset of disease (see, e.g. FIG. 2). Thus, the data provided herein indicate that analyzing the PAI-1 level and/or activity is not only useful for identifying an existed PPCM, but also for identifying a risk for developing PPCM (before onset of the disease).

As indicated above, the appended Examples demonstrate that the PAI-1 level is indicative for PPCM. Thus, one aspect of the present invention relates to the diagnosis of PPCM by analyzing (i.e. measuring/determining) the amount of the PAI-1 protein (e.g. in the blood plasma or serum). Accordingly, a preferred aspect of the invention relates to a method for identifying a subject, which has PPCM or which has a risk for developing PPCM, wherein the method comprises:
(a) analyzing (i.e. measuring/determining) in a sample obtained from a test subject the amount of PAI-1;
(b) comparing said amount with reference data corresponding to the amount of PAI-1 of at least one reference subject; and
(c) identifying a subject, which has PPCM or which has a risk for developing PPCM based on the comparison step (b).

In particular, if the reference subject does not have PPCM, then an increased amount of the PAI-1 of the test subject as compared to the reference data (i.e. the reference value(s)) indicates the presence of PPCM or a risk for developing PPCM. On the other hand, if the reference subject has PPCM, then an identical or similar amount of the PAI-1 of the test subject as compared to the reference data (i.e. the reference value(s)) indicate the presence of PPCM or a risk for developing PPCM.

The amount of PAI-1 (i.e. the amount of PAI-1 protein) can be analyzed, e.g., as described in the appended Examples (see, e.g. FIGS. 1 and 2). In particular, the amount of PAI-1 can be analyzed by the Quantikine ELISA human total serpine E1/PAI-1 Immunoassay from R&D systems [catalog number DTSE100] according to the manufacturer's protocol. Serum and plasma samples are preferably measured in duplicates. In all measurements internal controls, i.e. a specified sample from a postpartum control (that does not have PPCM) and from a PPCM patient are preferably used for internal calibration and comparison.

The illustrative appended Examples demonstrate that also the PAI-1 activity (particularly the PAI-1/16K prolactin/tPa/uPA/uPAR-mediated NF-kB activity) is increased in women with PPCM (see, e.g. FIG. 3). In particular, the appended Examples show that sera of women with PPCM activate NF-kB (nuclear factor 'kappa-light-chain-enhancer' of activated B-cells) considerably stronger as compared to sera of healthy women (see, e.g. FIG. 3). This activation could almost completely be inhibited by a siRNA against urokinase-type plasminogen activator receptor, demonstrating that this stronger NF-kB activation is mediated through uPAR (see, e.g. FIG. 3).

Without being bound by theory, it is believed that the increase in NF-kB activation in PPCM women is mediated via a complex comprising PAI-1, 16K prolactin, tPA and urokinase-type plasminogen activator (uPA), which binds to and activates uPAR. It is thought that within this complex PAI-1 changes its function from an uPAR inhibitor to a strong activator of uPAR. After activation through PAI-1, uPAR effects activation of NF-kB. Without being bound by theory, it is believed that the canonical function of PAI-1 binding to tPA and subsequently to uPAR is to repress uPAR mediated fibrinolysis and thereby increases thrombotic activity. If bound to 16K prolactin PAI-1 seems to promote fibrinolyes and with this becomes an antithrombotic factor (Bajou, 2014, Nat Med. 20(7):741-7), a feature that may explain why prolactin blockers such as bromocriptine may increase the thrombotic risk. However, the appended Examples indicate that complexed with 16K prolactin PAI-1 becomes also an activator of NF-kB and with this a PPCM promoting factor. Accordingly, the illustrative appended Examples indicate that development and progression of PPCM is associated with increased PAI-1 levels while improvement is associated with a decline in PAI-1 and suggest that PAI-1 activation may be causally involved in PPCM (see, e.g. FIGS. 1 and 2). Accordingly, an aspect of the invention relates to the diagnosis of PPCM by analyzing (i.e. measuring/determining) the activity of PAI-1 (e.g. in the blood serum). Thus, the invention relates to a method for identifying a subject, which has PPCM or which has a risk for developing PPCM, wherein the method comprises:

(a) analyzing (i.e. measuring/determining) in a sample obtained from a test subject the activity of PAI-1;

(b) comparing said activity with reference data corresponding to the activity of PAI-1 of at least one reference subject; and (c) identifying a subject which has PPCM or which has a risk for developing PPCM based on the comparison step (b).

In particular, if the reference subject does not have PPCM, then an increased activity of the PAI-1 (i.e. an increased uPAR-mediated NF-kB activity) of the test subject as compared to the reference data (i.e. the reference value(s)) indicates the presence of PPCM or a risk for developing PPCM. On the other hand, if the reference subject has PPCM, then an identical or similar activity of the PAI-1 (i.e. an identical or similar uPAR-mediated NF-kB activity) of the test subject as compared to the reference data indicate the presence of PPCM or a risk for developing PPCM.

The PAI-1 activity can be analyzed by measuring the uPAR-mediated NF-kB activity. In particular, cells (e.g. endothelial cells, such as RHE-A) may be transfected with a NF-kB reporter construct (e.g. a NF-kB luciferase reporter construct). As a control, also cells with uPAR knockdown may be used. The transfected cells may be stimulated with a composition comprising a sample obtained from the subject to be tested (i.e. the test subject). For example, the transfected cells may be stimulated with blood serum obtained from a subject to be tested. Then, the uPAR-mediated NF-kB activity may be measured. For example, the uPAR-mediated NF-kB activity may be measured by measuring luciferase activity using the Varioskan Flash Top/Bottom, Thermo Scientific (catalogue number: 5250040). The uPAR-mediated NF-kB activity is then determined by comparing the NF-kB activity of the control (uPAR knockdown) cells with the NF-kB activity of the cells expressing uPAR. In addition, PAI-1 inhibitors such as PAI-039 can be used to confirm that serum induced NF-kB activity is mediated via PAI-1.

This cell-based test system may also be used for preclinical screening for small molecules that block PAI-1/16K prolactin, tPA/uPA/uPAR-mediated NF-kB activation.

In the herein provided diagnostic method, the PAI-1 activity (as analyzed by measuring the uPAR-mediated NF-kB activity) obtained for a sample of the test subject may be compared with the PAI-1 activity obtained for a sample of a reference subject (i.e. control subject). Therefore, cells (e.g. endothelial cells, such as RHE-A), particularly wild-type and with uPAR knockdown, may be transfected with a NF-kB reporter construct (e.g. a NF-kB luciferase reporter construct). The transfected cells may be stimulated with a composition comprising either a sample obtained from the subject to be tested (i.e. the test subject) or a sample from a reference subject (i.e. the control subject). For example, the transfected cells may be stimulated with blood serum either obtained from a subject to be tested or from a reference subject (e.g. a healthy postpartal woman). Then, the NF-kB activity may be measured, e.g. by measuring luciferase activity. The uPAR-mediated NF-kB activity is then determined by comparing the NF-kB activity of the control (uPAR knockdown) cells with the NF-kB activity of the cells expressing uPAR. Afterwards, the uPAR-mediated NF-kB activity, which was measured in the RHE-A cells, which were stimulated with the sample obtained from the test subject is determined by comparison to the NF-kB activity, which was measured in the cells, which were stimulated with the sample obtained from the reference subject.

An increase in PAI-1 levels can result from genetic PAI-1 polymorphisms (Gils, 2004, Thromb Haemost. 91(3):425-37). Accordingly, an abnormal genotype of the PAI-1 gene may be causative for increased PAI-1 levels and the development of PPCM. Therefore, one aspect of the invention relates to the diagnosis of PPCM by analyzing (i.e. measuring) the genotype of the PAI-1 gene. Thus, the invention relates to a method for identifying a subject which has PPCM or which has a risk for developing PPCM, wherein the method comprises:

(a) analyzing in a sample obtained from a test subject the genotype of the PAI-1 gene;

(b) comparing said genotype of the PAI-1 gene with reference data corresponding to the genotype of the PAI-1 gene of at least one reference subject; and (c) identifying a subject which has PPCM or which has a risk for developing PPCM based on the comparison step (b).

In particular, if the reference subject does not have PPCM, then a different genotype of the PAI-1 gene of the test subject as compared to the reference data indicates the presence of PPCM or a risk for developing PPCM. On the other hand, if the reference subject has PPCM, then the same genotype of the PAI-1 gene of the test subject as compared to the reference data indicates the presence of PPCM or a risk for developing PPCM.

The genotype of the PAI-1 gene can be analyzed by sanger sequencing of the DNA samples isolated from full blood or blood clot of PPCM subjects and reference subjects.

Accordingly, in the herein provided method for identifying a subject, which has PPCM or which has a risk for developing PPCM, the amount and/or the activity of PAI-1 and/or the genotype of the PAI-1 gene may be analyzed. Preferably, the amount and/or the activity of PAI-1 is/are analyzed in the herein provided diagnostic method. Most preferably, the amount of PAI-1 is analyzed in the herein provided diagnostic method.

Thus, one aspect of the invention relates to a method for identifying a subject, which has PPCM or which has a risk for developing PPCM, wherein the method comprises:

(a) analyzing (i.e. measuring/determining) in a sample obtained from a test subject
  (a1) the amount and/or activity of PAI-1; and/or
  (a2) the genotype of the PAI-1 gene;

(b) comparing
  (b1) said amount and/or activity with reference data corresponding to the amount and/or activity of PAI-1 of at least one reference subject; and/or
  (b2) said genotype of the PAI-1 gene with reference data corresponding to the genotype of the PAI-1 gene of at least one reference subject; and (c) identifying a subject, which has PPCM or which has a risk for developing PPCM based on the comparison step (b).

In the herein provided diagnostic method, the reference subject may be a person who does not have PPCM (i.e. a healthy postpartum woman). Preferably, more than 10 (e.g.

20) reference subjects are used. Thus, one aspect of the invention relates to the above described diagnostic method of the invention, wherein at least one (preferably more than 10, e.g. the 20) reference subject(s) do(es) not have PPCM; and wherein in step (c)
  (c1) an increased amount and/or activity of PAI-1 of the test subject as compared to the reference data indicates the presence of PPCM or a risk for developing PPCM; and/or
  (c2) a different genotype of the PAI-1 gene of the test subject as compared to the reference data indicates the presence of PPCM or a risk for developing PPCM.

The appended Examples demonstrate that in women who suffer from PPCM the amount of PAI-1 in the blood plasma and serum (i.e. the sum of complexed and non-complexed PAI-1) is increased by about 3 times as compared to healthy postpartum women (see, e.g. FIG. 1). In particular, the appended Examples show that in women with PPCM, the average amount of PAI-1 in the blood plasma is 72 ng/ml. In contrast, in healthy postpartum women, the average amount of PAI-1 in the blood plasma is only 24 ng/ml. Therefore, in the herein described diagnostic method a subject (preferably a postpartum human women) is identified as having PPCM or as having a risk for developing PPCM if the amount of PAI-1 is increased in the sample of the test subject as compared to a sample of the reference subject (preferably a postpartum human women) which does not have PPCM (i.e. a healthy subject). For example, if the sample is a blood plasma sample (preferably an EDTA blood plasma sample), then a test subject is identified has having PPCM or as having a risk for developing PPCM if the amount of PAI-1 in the sample is ≥25 ng/ml, preferably ≥40 ng/ml, more preferably ≥50 ng/ml, and even more preferably ≥55 ng/ml (e.g. 65 ng/ml). If the sample is a blood serum sample, then a test subject is identified as having PPCM or as having a risk for developing PPCM if the amount of PAI-1 in the sample is ≥90 ng/ml, preferably ≥120 ng/ml, and even more preferably ≥150 ng/ml (e.g. ≥91 ng/ml) since the average amount of PAI-1 in blood serum is 157 ng/ml. In contrast, in healthy postpartum women, the average amount of PAI-1 in the blood serum is only 61 ng/ml. Or, in other words, a test subject is identified as having PPCM or as having a risk for developing PPCM if the amount of PAI-1 in the sample (e.g. in the blood plasma or serum samples) is at least 110%, preferably at least 125%, more preferably at least 170%, more preferably at least 200%, and even more preferably at least 230% (e.g. at least 200%) of the amount of PAI-1 in the sample of the reference subject which does not have PPCM.

In context of the present invention "PAI-1 activity" is defined as uPAR-mediated NF-kB activity (particularly PAI-1/16K prolactin/uPA-mediated NF-kB activity). Or, in other words, the "PAI-1 activity" can be measured by measuring the amount of NF-kB activated by PAI-1 and the uPAR system. Therefore, herein the PAI-1 activity reflects the ability of the sample to activate NF-kB. It is shown in the appended Examples (particularly FIG. 3) that blood serum samples of healthy postpartum women display enhanced activation of NF-kB within the first 3 days postpartum. Thereafter, activation of NF-kB is constantly low in healthy postpartum women. In contrast, in serum form PPCM patients, collected at least 2 weeks after delivery, the average PAI-1 (i.e. uPAR)-mediated NF-kB activity is at least 1.5-fold higher compared to healthy postpartum women. In the herein described diagnostic method a test subject (preferably a postpartum human woman) is identified as having PPCM or as having a risk for developing PPCM if the activity of PAI-1 is increased in the sample (preferably a blood serum sample) of the test subject as compared to a sample of a reference subject (preferably a postpartum human woman), which does not have PPCM (i.e. a healthy subject). For example, a test subject is identified has having PPCM or as having a risk for developing PPCM if the PAI-1 activity (particularly the uPAR-mediated NF-kB activity) in the sample is at least 125%, preferably at least 140%, more preferably 150%, more preferably at least 170%, more preferably at least 200%, and even more preferably at least 230% (e.g. at least 200%) of the activity of PAI-1 in the sample of the reference subject which does not have PPCM. It is described above that it can be analyzed whether the NF-kB activity is mediated by the PAI-1/uPAR system. This is preferably done by comparing the measured NF-kB activity of cells having uPAR knockdown with cells expressing uPAR. In this regard, the uPAR deficient cells (i.e. the cells having an uPAR knockdown) show a similar NF-kB activity for all samples (i.e. for the PPCM and the reference sample). In this context, the term "similar" refers to values that do not differ more that 20% from each other. In addition, PAI-1 inhibitors such as PAI-039 (that is also known as tiplaxtinin, CAS Registry Number: 393105-53-8) can be used to confirm that serum induced NF-kB activity is mediated via PAI-1 (see, e.g. FIG. 3).

Accordingly, in the herein described diagnostic method, if the reference subject does not have PPCM, an amount and/or activity of the PAI-1 activity (particularly the uPAR-mediated NF-kB activity) of the test subject which is at least 125% of the reference data indicates the presence of PPCM or a risk for developing PPCM. In addition, if the reference subject does not have PPCM, an amount of PAI-1 of the test subject which is preferably at least 170%, more preferably at least 200%, and even more preferably at least 230% (e.g. at least 200%) of the reference data indicates the presence of PPCM or a risk for developing PPCM. Furthermore, if the reference subject does not have PPCM, an PAI-1 activity (particularly an uPAR-mediated NF-kB activity) of the test subject, which is preferably at least 125%, and more preferably at least 140% of the reference data indicates the presence of PPCM or a risk for developing PPCM.

In the herein described and provided diagnostic method, the "reference subject" is not necessarily a healthy subject. In particular, the reference subject can also be a subject (preferably a postpartum human woman), which has PPCM (i.e. a diseased subject). If in the herein described diagnostic method the reference subject has PPCM, then an identical or similar amount and/or activity of PAI-1 (particularly uPAR-mediated NF-kB activity) of the test subject as compared to the reference subject indicate the presence of PPCM or a risk for developing PPCM. Thus, the invention relates to the herein described diagnostic method, wherein the at least one reference subject has PPCM; and wherein in step (c) an identical or similar amount and/or activity of PAI-1 of the test subject as compared to the reference data indicates the presence of PPCM or a risk for developing PPCM. The reference subject may also have PPCM that is caused by a particular genetic predisposition. Accordingly, the invention also relates to the herein described diagnostic method, wherein the at least one reference subject has PPCM; and wherein in step (c) the same genotype of the PAI-1 gene of the test subject as compared to the reference data indicates the presence of PPCM or a risk for developing PPCM.

The appended Examples show that in women, which have PPCM the amount of PAI-1 in the blood plasma sample is about 72±42 ng/ml (mean±standard derivation, p<0.0001), see, e.g. FIG. 1. Accordingly, in women with PPCM the amount of PAI-1 can vary to a certain degree. However, in about 85% of the women with PPCM the amount of PAI-1 in plasma was higher than 40 ng/ml. Therefore, in the herein described diagnostic method, a test subject is identified has having PPCM or as having a risk for developing PPCM if the amount of PAI-1 in the sample (e.g. in the blood plasma or serum sample) of the test subject is at least 50-140%, preferably at least 70-130%, more preferably at least 80-120%, and even more preferably at least 90-110% of the amount of PAI-1 in the sample of the reference subject, which has PPCM.

It is further shown in the appended Examples that in samples of women with PPCM, the activity of PAI-1 (i.e. the ability of the sample to activate NF-kB) is about 280±124% (mean±standard derivation) compared to healthy postpartum women (that are at least two weeks postpartum), see, e.g. FIG. 3. Accordingly, in women with PPCM the activity of PAI-1 can vary to a certain degree. Therefore, in the herein described diagnostic method, a test subject is identified has having PPCM or as having a risk for developing PPCM if the activity of PAI-1 in the sample of the test subject is at least 75-125%, preferably at least 80-120%, and more preferably at least 90-110% of the activity of PAI-1 in the sample of the reference subject which has PPCM.

The herein provided diagnostic method comprises the measurement of the amount of PAI-1 and the activity of PAI-1 (i.e. the NF-kB activity mediated by PAI-1 and the uPAR system). The amount of PAI-1 can be determined in several ways. For example, the amount of the messenger RNA (mRNA) encoding PAI-1 or the amount of the expressed PAI-1 protein can be measured. Thus, step (a1) of the herein described diagnostic method comprises analyzing the amount of the PAI-1 protein and/or analyzing the activity of the PAI-1 protein (i.e. its ability to activate NF-kB) and/or analyzing the amount of the PAI-1 RNA. The nucleotide sequence of the mRNA of PAI-1 is shown in SEQ ID NO: 1, the amino acid sequence of the PAI-1 protein is shown in SEQ ID NO: 2. Preferably, the amount and/or activity of the PAI-1 protein is analyzed in step (a1) of the herein provided diagnostic method. The amount of a protein can be measured by several methods, e.g., Enzyme Linked Immunosorbent Assay (ELISA) or Western Blot. Herein, it is preferred that the amount of PAI-1 is analyzed by ELISA. The technical procedure of an ELISA is commonly known in the art and described, in the Manufactor's protocol of the ELISA used. For the ELISA a commercially available ELISA kit (e.g. Quantikine ELISA, Human Total Serpine E1/PAI-1, Catalog Number DTSE100, R&D-Systems) may be used. Indeed, in the appended Examples the Quantikine ELISA, Human Total Serpine E1/PAI-1 (Catalog Number DTSE100, R&D-Systems) was successfully performed according to the instructions of the manufacturer to measure plasma and serum PAI-1 levels.

The prior art describes that genetic aberrations such as genetic PAI-1 polymorphisms can lead to increased PAI-1 levels (Gils, 2004, Thromb Haemost. 91(3):425-37). In context of the present invention it has been shown that such increased PAI-1 levels are indicative for the existence and the development of PPCM. Therefore, it is plausible that genetic aberrations of the PAI-1 gene can directly indicate the presence of PPCM or the risk for developing PPCM. However, the appended Examples demonstrate that women with PPCM have no increased incidence of the known PAI-1 polymorphisms −675 5G/5G, −675 4G/4G, −844G/-844G; and A-844/A-844 (see, e.g. FIG. 4), which however, does not rule out the presence of additional polymorphism that may affect PAI-1 expression and/or stability. Specifically polymorphisms within the promoter region have been described, which include a 4G/5G polymorphism at position −675 and a base substitution of A to G at position −844 (A-844-G), which appear to influence the gene expression level and may lead to a higher risk of thrombotic complications such as stroke and myocardial infarction, respectively miscarriages (Declerck, 2013, Semin Thromb Hemost. 39(4):356-64; Chen, 2015. Am J Reprod Immunol. 73(4):292-300). Moreover, as shown in the illustrative appended Examples (see, e.g. FIG. 4), an additional polymorphism (substitution of C to T) was found at position −747 of the PAI-1 promoter (see FIG. 6). This polymorphism was only present in a PPCM patient who had continuously high PAI-1 serum levels even after delivery and during a subsequent pregnancy suggesting that it may be of relevance for PPCM. Thus, the invention relates to the herein described diagnostic method, wherein in step (c) the presence of a genetic polymorphism or a mutation in the PAI-1 gene in the sample of the test subject indicates the presence of PPCM or a risk for developing PPCM, wherein said genetic polymorphism or mutation is a C to T substitution at position −747 of the PAI-1 promoter. Other genetic polymorphisms that are useful for diagnosing PPCM are genetic polymorphisms in the PAI-1 gene that affect expression and stability in the context of pregnancy. In addition, the mutation in the PAI-1 gene is preferably an activating mutation leading either to higher protein amounts, better mRNA or protein stability and/or better binding of 16K prolactin. Polymorphisms affecting mRNA stability and protein translation are of special interest since PAI-1 is the target of several microRNAs. In the herein provided methods, the genotype may be determined by sanger sequencing on the whole genomic DNA of the PAI-1 gene.

Healthy, young women with no previous signs of heart disease can develop PPCM very suddenly. The present inventors surprisingly found that increased PAI-1 levels occur during the development of PPCM. Therefore, it is plausible that PPCM develops in women, which have a genetic predisposition for PPCM (e.g. a polymorphism or a mutation in the PAI-1 gene), which is inducible by pregnancy hormones, birth hormones and/or stress factors. Or, in other words, it is plausible that during pregnancy and/or delivery specific polymorphisms or mutations in the PAI-1 gene are induced by pregnancy hormones, birth hormones and/or stress factors and subsequently lead to an increased PAI-1 level, which then contributes to the development of PPCM. Thus, the invention relates to the herein described diagnostic method, wherein in step (c) the presence of a genetic polymorphism or a mutation in the PAI-1 gene, which is inducible by pregnancy hormones, birth hormones and/or stress factors indicates the presence of PPCM or a risk for developing PPCM.

As described above, it is plausible that a genetic predisposition (i.e. a genetic aberration within the PAI-1 gene) causes PPCM. Therefore, the inventive diagnostic method (in particular the analysis of the genotype in steps (a2), (b2) and (c)) can be carried out during the whole life of the subject to be tested. However, the onset of PPCM (i.e. the onset of symptoms) occurs during pregnancy, up to seven month after the baby is born. Therefore, the invention relates to the herein described diagnostic method, wherein the time point for obtaining the sample was between the beginning of pregnancy and seven months postpartum. Mostly, PPCM develops between the last month of pregnancy and seven months after the baby is born. Therefore, it is preferred in the herein provided diagnostic method that the time point for obtaining the sample was within this range. Preferably, the time point for obtaining the sample was in this range, i.e.

during the first days after delivery and seven months after delivery. For the patient an early diagnosis of PPCM is advantageous. Therefore, the time point for obtaining the sample was more preferably between day 2 after delivery up to seven months after postpartum. Most preferably, the time point for obtaining the sample was:

(a1) between 1 day and 7 month after delivery if the amount of PAI-1 is analyzed; and/or (a2) between 2 weeks and 7 month after delivery if the activity of PAI-1 is analyzed.

The appended Examples demonstrate that in a woman with a high risk for PPCM due to a PPCM in a previous pregnancy, PAI-1 levels are higher compared to healthy postpartum women even before onset of disease (see, e.g. FIGS. 2 and 3). However, it is envisaged in context of the inventive diagnostic method that the time point for obtaining the sample was (or was nearby) the time point when the symptoms of PPCM started (i.e. the time point when the diseased women first communicated the symptoms of PPCM to her physician).

In context of the present invention it has been identified that in healthy women who are pregnant directly before delivery the PAI-1 levels are increased as compared to non-pregnant, non-postpartal women but is already markedly decreased and substantially lower than in women with PPCM 1 day and even lower 2 days after delivery (see, e.g. FIG. 1). In addition, the present inventors identified that the PAI-1 levels are higher in patients with PPCM at the time point of diagnosis independent of the relation to the time point of delivery while PAI-1 levels are lower in healthy postpartum women at all time points. Therefore, in the diagnostic method provided herein, the test subject may be compared with reference data corresponding to the amount and/or activity of PAI-1 of at least one reference subject, wherein the reference subject is also a woman who is 2 weeks till 7 months postpartum.

An advantage of the herein described diagnostic method is that it can be performed as a part of the preventive examinations, e.g. within the second week after delivery. Preferably, in a first screen PAI-1 plasma and/or serum levels are determined as early as 1 day after delivery for identifying a risk for PPCM and are more preferably combined with an activity test for PAI-1 (i.e. uPAR-mediated NF-kB activation) as early as 2 weeks after delivery thereby confirming the risk or presence for PPCM. Thus, the inventive diagnostic method can represent a routine check-up, which easily and fast diagnoses PPCM at an early stage. Particularly women with risk factors for PPCM can profit from the inventive diagnostic method as these women have a relatively high probability for developing the disease. Therefore, it is envisaged in context of the diagnostic method provided herein to further analyze whether the subject to be tested has risk factors for PPCM. Accordingly, the present invention relates to the herein provided diagnostic method, further comprising identifying whether said test subject has at least one of the risk factors selected from overweight, smoking, twin pregnancy, pregnancy-induced or independent hypertensive disorder, the pregnancy was made by in vitro fertilization, high blood pressure, and receipt of chemotherapy before the pregnancy.

The determination of risk factors can be performed before or after analyzing the amount, activity and/or genotype of PAI-1. For example, the determination of risk factors can be performed before analyzing the amount, activity and/or genotype of PAI-1. In particular, the analysis of the amount, activity and/or genotype of PAI-1 can be performed if the woman has at least one (preferably at least two) of said risk factors. Alternatively, the determination of risk factors can be performed if PPCM has been diagnosed by analyzing the amount, activity and/or genotype of PAI-1 (e.g. in order to further validate the presence of PPCM, to establish an appropriate medication or to predict the outcome of the disease).

It is also envisaged in context of the diagnostic method provided herein to further analyze whether the subject to be tested has symptoms of PPCM. Accordingly, the present invention relates to the herein provided diagnostic method, further comprising identifying whether said test subject has at least one of the symptoms selected from orthopnea, dyspnea, pitting edema, cough, frequent night-time urination, excessive weight gain during the last month of pregnancy, palpitations, chest pain, depression, fatigue and physical weakness. For diagnostic confirmation echocardiographic analysis would be recommended in any case.

The determination of PPCM symptoms can be performed before or after analyzing the amount, activity and/or genotype of PAI-1. For example, the determination of PPCM symptoms can be performed before the analysis of the amount, activity and/or genotype of PAI-1 and the analysis of the amount, activity and/or genotype of PAI-1 can be performed if the woman has at least one (preferably at least two) of said symptoms. Alternatively, the determination of PPCM symptoms can be performed if PPCM has been diagnosed by analyzing the amount and activity of PAI-1 (e.g. in order to further validate the presence of PPCM, to establish an appropriate medication or to predict the outcome of the disease). Upon positive diagnostic values for increased PAI-1 plasma or serum levels and/or serum activity and confirmed PPCM diagnosis by echocardiography, genotype of the PAI-1 gene can be made for further risk stratification and genetic counseling.

In step (a) of the herein described diagnostic method for identifying a subject, which has PPCM or which has a risk for developing PPCM, a sample, which is obtained from the subject to be tested is analyzed. In particular, the amount and/or activity of PAI-1 and/or the genotype of the PAI-1 gene is/are analyzed in said sample of the subject to be tested. In step (b) of the inventive method, said amount, activity and/or genotype is compared to reference data corresponding to the PAI-1 amount, activity and/or genotype, respectively, of at least one reference subject. It is envisaged that said reference data corresponds to a "sample" of a reference subject. Or, in other words, said reference data may comprise the amount and/or the activity of PAI-1, which is present in a sample of a reference subject (e.g. a healthy postpartum woman). In line with this, said reference data may comprise the genotype of the PAI-1 gene, which is present in a sample of a reference subject (e.g. a healthy postpartum woman).

In the inventive diagnostic method, the sample can be blood, blood plasma, blood serum or urine. It has been confirmed in the appended Examples that, both, blood plasma as well as blood serum samples show a considerable different PAI-1 level in PPCM patients as compared to healthy women. In addition, the present inventors identified that the PAI-1 activity (e.g. the ability of PAI-1 to activate NF-kB) is substantially different in blood serum samples of women with PPCM as compared to healthy postpartum control women. Blood plasma is less preferred for uPAR-mediated NF-kB activity measurements since EDTA in these samples act inhibitory for the assay. Thus, if in the diagnostic method provided herein the PAI-1 activity is analyzed (i.e. measured/determined), then the sample is preferably blood serum. For analyzing (i.e. determining) the genotype of the PAI-1 gene the sample needs to be genomic DNA containing tissue or fluid of the body. For example, the sample may be blood, blood plasma, blood serum, urine, or blood clot. Preferably, the sample is blood clot.

Accordingly, the methods of the present invention have the advantage that only one blood sample has to be taken per subject in order to determine the PAI-1 amount, the PAI-1 activity and the genotype of the PAI-1 gene. More specifically, the PAI-1 amount (i.e. the PAI-1 level) is preferably analyzed in the blood plasma (or serum); the PAI-1 activity is preferably analyzed in the blood serum; and the genotype of the PAI-1 gene is preferably analyzed in the blood clot.

Figure 5:
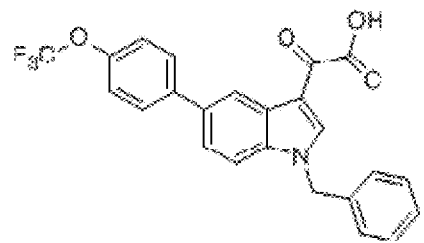
Figure 5:
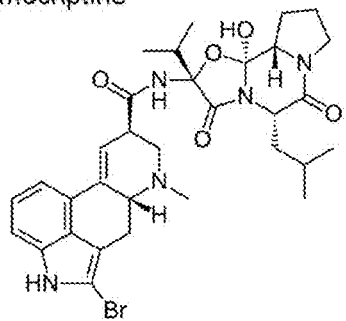

If by using the inventive diagnostic method a woman has been diagnosed as having PPCM, it is envisaged that this women is treated with an appropriate medication. Thus, the invention relates to the herein provided diagnostic method, wherein a medication for PPCM is to be administered to the subject, which has been identified as having PPCM or which has been identified as having a risk for developing PPCM. Or in other words, the invention relates to medication for PPCM for use in treating a subject which has been identified as having PPCM or which has been identified as having a risk for developing PPCM by the herein provided diagnostic method. For example, the subject, which has been identified as having PPCM or which has been identified as having a risk for developing PPCM (i.e. the PPCM diseased or PPCM prone subject) may be treated with bromocriptine. Bromocriptine is also known as 2-bromoergocryptine or bromocriptinum and has the formula $C_{32}H_{40}BrN_5O_5$. The structure of bromocriptine is shown in FIG. 5. Bromocriptine is an ergoline derivative, acts as a dopamine agonist and inhibits the secretion of prolactin. In the prior art, good results could be achieved by administering to PPCM patients bromocriptine in combination with usual medication for heart failure (e.g., beta-blockers, ACE inhibitors or diuretics). Thus, one aspect of the invention relates to the herein provided diagnostic method, wherein a medication for PPCM is to be administered to the subject, which has been identified as having PPCM or which has been identified as having a risk for developing PPCM, and wherein said medication comprises of bromocriptine given together with at least prophylactic anticoagulation, and optionally also given together with a beta blocker, an ACE inhibitor, and if needed a diuretic. Preferably, said medication comprises a combination of bromocriptine given together with at least prophylactic anticoagulation, and optionally also given together with beta-blocker, an ACE inhibitor, and if needed a diuretic.

Moreover, in context of the present invention it has been surprisingly found that PAI-1 levels are increased in PPCM patients and that PAI-1 mediates extensive NF-kB activation. NF-kB activation in PPCM has been shown via miR146a to mediate a substantial part of the pathophysiology in PPCM diseased women. Accordingly, these data indicate that PAI-1 represents a crucial player in the development and progression of PPCM. Thus, inhibition of PAI-1 may directly target the pathology (i.e. the cause) of PPCM. Directly targeting the factors, which are causative for PPCM development and progression may result in a faster recovery of the diseased women. This would promote fast recovery thereby minimizing subclinical cardiac injury and invasive medication against heart failure, which considerably impact on quality of life of these usually young women and their families. The appended Examples demonstrate that treatment with bromocriptine is associated with a substantial decrease in PAI-1 level and an increase in cardiac function (see, e.g. FIG. 2). Without being bound by theory, the reason may be that treatment with bromocriptine stops secretion of prolactin and with this also the generation of 16K prolactin, the binding partner for PAI-1 with regard to NF-kB activation. Moreover, the appended Examples also show that pharmacological inhibition of PAI-1 in serum of PPCM patients by PAI-039 decreases NF-kB activation (see, e.g. FIG. 3). Thus, both observations support the idea of PAI-1 as being an active factor in initiating and driving PPCM.

Thus, the invention relates to an inhibitor of PAI-1 for use in the treatment of PPCM, wherein said inhibitor is
(a) a RNA interference molecule, preferably an siRNA or an shRNA;
(b) an antibody, which specifically binds to PAI-1; or
(c) PAI-039.

The above described PAI-1 inhibitor may also be
(d) an inhibitor of NF-kB; or
(e) a molecule, which blocks in PAI-1 the binding site for 16K prolactin.

For example, in context of the present invention, the antibody, which specifically binds to PAI-1 may be one of the PAI-1 inhibiting monoclonal antibodies disclosed in Gils (2004, Thromb Haemost. 91(3):425-37). The RNA interference molecule, which is directed against the mRNA of PAI-1 may be a siRNA against PAI-1 as disclosed in US 2013/0035289 A1. The RNA interference molecule, which is directed against the mRNA of PAI-1 may also be the siRNA or shRNA directed against PAI-1 as disclosed in WO 2012/129513 A1. However, also the PAI-1 inhibiting peptides as described in US2013/0035289A1 or Gils (2004, Thromb Haemost. 91(3):425-37) or the PAI-1 inhibiting low molecular weight compounds or detergents as disclosed in Gils (2004, Thromb Haemost. 91(3):425-37) may be used according to the invention in the treatment of PPCM. The inhibitor of NF-kB is preferably curcumin, a natural compound of Curcuma longa.

Thus, the present invention provides a new medication for the treatment of PPCM. This medication can be combined with conventional medications for PPCM, such as bromocriptine, diuretics, ACE inhibitors and/or beta-blockers. Combining several different medicaments in the treatment of PPCM has the advantage that the doses of the individual medicaments can be reduced without a significant loss of therapeutic activity. Or, in other words, the provision of a further medicament, which is useful in the treatment of PPCM (i.e. a PAI-1 inhibitor and/or an NF-kB inhibitor) has the advantage that in a combined therapy lower doses of the different medicaments can be used. Using a lower dose of a medicament has the advantage that it is easier to not exceed the maximum tolerated dose (i.e. the highest dose of the medicament that will produce the desired effect without unacceptable toxicity).

Accordingly, one aspect of the invention relates to the herein provided diagnostic method, wherein a medication for PPCM is to be administered to the subject, which has been identified as having PPCM or which has been identified as having a risk for developing PPCM, wherein said medication comprises at least one of the inhibitors of PAI-1 as indicated above under items (a) to (e), preferably at least one of the inhibitors of PAI-1 as indicated above under (a) to (c). It is preferred that said medication comprises a combination of at least one of the inhibitors of PAI-1 as indicated above under items (a) to (e), (more preferably at least one of the inhibitors of PAI-1 as indicated above under (a) to (c)) and the active agent selected from bromocriptine with anticoagulation, a beta blocker, an ACE inhibitor, and if needed a diuretic.

PAI-039 is also known as tiplaxtinin (CAS Registry Number: 393105-53-8) and its IUPAC formula is [1-Benzyl-5-(4-trifluoromethoxy)phenyl)-1H-indol-3-yl]-oxoacetic acid. The structure of PAI-039 is shown in FIG. 5. PAI-039 is preferably administered orally. For example, pharmaceutical compositions comprising PAI-039 may be in a form of (a) powder(s), (an) aerosol(s), (a) solution(s), or preferably (a) tablet(s). A molecule, which blocks in PAI-1 the binding site for 16K prolactin would obviate the complex formation between PAI-1 and 16K prolactin, and thus, may inhibit PAI-1 activity. Several inhibitors of NF-kB are known in the art. Preferably, the NF-kB inhibitor used in the context of the present invention is curcumin.

As described above, inhibition of PAI-1 represents a promising treatment for PPCM. Thus, the invention relates to a treatment method, in particular to method of treating PPCM in a subject in need of such a treatment, wherein said method comprises administering to said subject an effective amount of at least one of the inhibitors of PAI-1 as indicated above under items (a) to (e), (preferably at least one of the inhibitors of PAI-1 as indicated above under (a) to (c)), wherein said subject has been identified as having PPCM or as having a risk for developing PPCM by using the diagnostic method of the invention. For example, one aspect of the above described inventive treatment method relates to a method of treating PPCM in a subject in need of such a treatment, wherein said method comprises administering to said subject an effective amount of at least one of the inhibitors of PAI-1 as indicated above under items (a) to (d), (preferably the inhibitors of PAI-1 as indicated above under items (a) to (c)), wherein said subject has an increased amount and/or activity of PAI-1 as compared to a reference subject, which does not have PPCM.

One aspect of the invention relates to the herein provided treatment method, wherein said method further comprises administering to said subject an effective amount of at least one of the active agents selected from bromocriptine, a beta blocker, an ACE inhibitor, and a diuretic. A preferred aspect of the invention relates to the herein provided treatment method, wherein said method comprises administering to said subject an effective amount of a combination of at least one of the inhibitors of the PAI-1 as indicated above under items (a) to (e), (more preferably at least one of the inhibitors of PAI-1 as indicated above under (a) to (c)) and at least one active agent selected from bromocriptine, a beta blocker, an ACE inhibitor, and a diuretic.

One aspect of the invention relates to the herein provided treatment method, wherein said test subject has an increased amount of PAI-1 in the blood plasma or blood serum (i.e. in a blood plasma sample or a blood serum sample) as compared to a reference subject, which does not have PPCM; and/or wherein said test subject has an increased activity of PAI-1 in the blood serum (i.e. in a blood serum sample) as compared to a reference subject, which does not have PPCM. In addition or alternatively, said test subject may have a genetic polymorphism in the PAI-1 gene. A genetic polymorphism of PAI-1, which may be detected in context of the herein provided diagnostic method or treatment method is the C to T polymorphism at position −747 of the PAI-1 promoter.

As indicated above, in the herein provided treatment method, the patient to be treated may be identified by the herein provided method for identifying a subject, which has PPCM or which has a risk for developing PPCM. Thus, one aspect of the above described inventive treatment method relates to a method of treating PPCM in a subject in need of such a treatment, wherein said method comprises administering to said subject an effective amount of at least one of the inhibitors of PAI-1 as indicated above under items (a) to (d), (preferably the inhibitors of PAI-1 as indicated above under (a) to (c)), wherein said subject has been identified as having PPCM or as having a risk for developing PPCM, wherein the method comprises:

(a) analyzing (i.e. measuring/determining) in a sample obtained from a test subject the amount and/or activity of PAI-1;

(b) comparing said amount and/or activity with reference data corresponding to the amount and/or activity of PAI-1 of at least one reference subject; and (c) identifying a subject, which has PPCM or which has a risk for developing PPCM based on the comparison step (b).

Preferably, the subject, which is treated in the herein provided treatment method has PPCM (i.e. is identified as having PPCM).

The present invention also relates to a pharmaceutical composition (i.e. a medicament) comprising at least one PAI-1 inhibitor as defined herein. The pharmaceutical composition of the invention may be in a form of (a) powder(s), (a) tablet(s), (an) aerosol(s) or (a) solution(s). If the pharmaceutical composition comprises PAI-039, then it is preferably in form of a tablet. If the pharmaceutical composition comprises a RNA interference molecule, then it is preferably in form of a solution. The pharmaceutical composition of the invention may be administered by different ways, e.g., parenteral, subcutaneous, intraperitoneal, topical, intrabronchial, intrapulmonary, intranasal or by infusion or injection. In particular, if the pharmaceutical composition comprises PAI-039, then it is preferably administered orally. However, if the pharmaceutical composition comprises a RNA interference molecule, then it is preferably administered via infusion or injection intravenously.

The pharmaceutical composition of the invention is administered to the subject at a suitable dose. The dosage regimen will be determined by the attending physician and clinical factors. As is well known in the medical arts, dosage for any single patient depends upon many factors, including the patient's size, body surface area, age, the particular compound (e.g. PAI-039 or similar, siRNA or shRNA) to be administered, sex, time and route of administration, general health, and other drugs being administered concurrently. However, the exact concentration will have to be determined in pharmacokinetics and pharmacodynamics studies following the code of federal regulations of the FDA.

The pharmaceutical compositions of the invention may further comprise pharmaceutical carriers, excipients and/or diluents. Suitable pharmaceutical carriers, excipients and diluents are well known in the art and include phosphate buffered saline solutions, water, emulsions, such as oil/water emulsions, various types of wetting agents, sterile solutions etc (see Remington's Pharmaceutical Sciences; 1980; 16th edition; Osol. A. Ed). Preservatives and other additives may also be present including, for example, antimicrobials, antioxidants, chelating agents, and inert gases and the like.

During the treatment of PPCM the success of therapy may be monitored by analyzing (i.e. determining/measuring) the amount and/or activity of PAI-1. Thus, the present invention relates to a method for monitoring the therapeutic success during the treatment of PPCM, wherein the method comprises:

(a) analyzing (i.e. determining/measuring) in a sample obtained from a test subject the amount and/or activity of PAI-1;

(b) comparing said amount and/or activity with reference data corresponding to the amount and/or activity of PAI-1 of at least one reference subject; and (c) predicting (i.e. assessing) the therapeutic success based on the comparison step (b).

In the herein provided monitoring method (i.e. in the herein provided method for monitoring the therapeutic success during the treatment of PPCM) the test subject is preferably a subject (e.g. a human woman), which receives medication for PPCM or which has received medication for PPCM.

One aspect of the invention relates to the herein provided monitoring method, wherein the at least one reference subject has PPCM but did not receive medication for PPCM; and wherein in step (c) an decreased amount and/or activity of PAI-1 of the test subject as compared to the reference data indicates therapeutic success in the treatment of PPCM.

Another aspect of the invention relates to the herein provided monitoring method, wherein the at least one reference subject has PPCM and has received medication for PPCM; and wherein in step (c) an identical or similar amount and/or activity of PAI-1 of the test subject as compared to the reference data indicates therapeutic success in the treatment of PPCM.

A further aspect the present invention relates to the herein provided monitoring method, wherein the at least one reference subject does not have PPCM; and wherein in step (c) an identical or similar amount and/or activity of PAI-1 of the test subject as compared to the reference data indicates therapeutic success in the treatment of PPCM.

In the herein provided monitoring method, the reference data preferably corresponds to the amount and/or activity of PAI-1 in a sample of the reference subject. In the herein provided monitoring method, "identical or similar amount of PAI-1" means that the amount of PAI-1 in the sample (e.g. in the blood plasma or serum sample) of the test subject is 60-140%, preferably 70-130%, more preferably 80-120%, and even more preferably 90-110% of the amount of PAI-1 in the sample of the reference subject. In addition, in the herein provided monitoring method, "identical or similar activity of PAI-1" means that the activity of PAI-1 in the sample of the test subject (e.g. the ability of the sample to activate NF-kB) is 75-125%, preferably 80-120%, more preferably 90-110% of the activity of PAI-1 in the sample of the reference subject.

The definitions (particularly regarding the analysis of the amount and the activity of PAI-1) disclosed herein in connection with the diagnostic method of the present invention (i.e. the method for identifying a subject, which has PPCM or which has a risk for developing PPCM) apply, mutatis mutandis, to the monitoring method described above.

As indicated, in the therein provided monitoring method the amount and/or activity of PAI-1 can be analyzed (i.e. determined/measured). Preferably, the PAI-1 amount is analyzed in the herein provided monitoring method.

In context of the present invention it has surprisingly and unexpectedly been found that an increased amount or activity of PAI-1 is indicative for the presence of PPCM. In order to determine whether the amount of PAI-1 is increased, binding molecules, which specifically bind to the PAI-1 protein or to the mRNA of PAI-1 can be used. In order to determine whether the activity of PAI-1 is increased, binding molecules, which specifically bind to the PAI-1/16K prolactin complex may be used. Thus, one aspect of the invention relates to the use of a binding molecule for identifying a subject, which has PPCM or which has a risk for developing PPCM, wherein said binding molecule specifically binds to at least one of the molecules defined in (a) to (c):

(a) PAI-1 (i.e. the PAI-1 protein);
(b) a nucleic acid molecule encoding the PAI-1 protein; or
(c) the PAI-1/16K prolactin complex.

The binding molecule, which specifically binds to the PAI-1 protein may be an anti-PAI-1 antibody (for example the human anti-PAI-1 Ab from R&D systems, Catalog #1786-PI and from Cell signaling, Catalog #11907). The binding molecule, which specifically binds to a nucleic acid molecule encoding the PAI-1 protein may be an oligonucleotide (i.e. an siRNA or shRNA designed by Biosprings or Darmacon). The production of such oligonucleotides is commonly known in the art and is performed according to the manufactors's protocol. The binding molecule, which specifically binds to the PAI-1/16K prolactin complex may be an antibody which specifically binds to PAI-1 or 16K prolactin. Preferably, two antibodies are used to detect the PAI-1/16K prolactin complex, i.e. an anti-PAI-1 antibody and an anti-16K prolactin antibody. For example, one of these antibodies (e.g. the PAI-1 antibody) may be used to isolate the PAI-1/16K prolactin complex (e.g. via immunoprecibitation) and the other antibody (e.g. the anti-16K prolactin antibody) may subsequently be used to detect (e.g. via Western Blot) the 16K prolactin within the isolated complex. Immunoprecipitation and Western Blot are commonly known methods, which are described for example in scbt.com/protocols.html?protocol=immunoprecipitation.

The binding molecules, which are in context of the invention used for identifying a subject, which has PPCM or which has a risk for developing PPCM can be part of a kit, which may be used to diagnose PPCM. Thus, the invention relates to the use of a kit for identifying a subject, which has PPCM or which has a risk for developing PPCM, wherein the kit comprises the binding molecule as defined herein above. The herein provided inventive diagnostic methods may be realized by using this kit. Advantageously, the kit of the present invention further comprises optionally (a) reaction buffer(s), storage solutions, wash solutions and/or remaining reagents or materials required for the conduction of the assays as described herein. Furthermore, parts of the kit of the invention can be packaged individually in vials or bottles or in combination in containers or multicontainer units. These vials/bottles/containers or multicontainers may, in addition to the binding molecules described herein, comprise preservatives or buffers for storage. In addition, the kit may contain instructions for use. The manufacture of the kit of the present invention follows preferably standard procedures which are known to the person skilled in the art. As mentioned above, the kit provided herein is useful for identifying a subject, which has PPCM or which has a risk for developing PPCM. Preferably, the kit provided herein is used for identifying a subject which has PPCM.

In context of the present invention it has surprisingly been identified that PAI-1 represents a biomarker and that this biomarker can be used to diagnose PPCM or a risk for developing PPCM. Thus, one aspect of the present invention relates to the use of the biomarker PAI-1 for diagnosing PPCM or for diagnosing a risk for developing PPCM. Preferably, the biomarker PAI-1 is used for diagnosing an existing PPCM.

Herein, the term "analyzing" also means "determining" or "measuring" (i.e. detecting and/or quantifying). For example, the term "analyzing the amount of PAI-1" means measuring the amount of PAI-1 (i.e. the amount of the PAI-1 protein). Methods for analyzing (i.e. measuring) the amount of the PAI-1 protein are known in the art and described herein above. Analogously, the term "analyzing the activity of PAI-1" means measuring the activity of PAI-1 (i.e. of the PAI-1 protein). In particular, to analyze the activity of PAI-1, NF-kB activation that is induced by PAI-1 via uPAR can be measured. Methods for analyzing the activity of the PAI-1 protein are known in the art and also described herein above.

The terms "treatment", "treating" and the like are used herein to generally mean obtaining a desired pharmacological and/or physiological effect. The effect may be prophylactic in terms of completely or partially preventing a disease or symptom thereof and/or may be therapeutic in terms of partially or completely curing a disease and/or adverse effect attributed to the disease. The term "treatment" as used herein covers any treatment of a disease in a subject and includes: (a) preventing and/or ameliorating a PPCM from occurring in a subject which may be predisposed to the disease; (b) inhibiting the disease, i.e. arresting its development like the inhibition of PPCM progression; or (c) relieving the disease, i.e. causing regression of the disease, like the repression of PPCM. Preferably, the term "treatment" as used herein relates to medical intervention of an already manifested disorder, like the treatment of an already defined and manifested PPCM.

For the purposes of the present invention the "subject" (or "patient") may be a female vertebrate. In context of the present invention, the term "subject" includes both humans and other animals, particularly mammals, and other organisms. Thus, the herein provided methods are applicable to both human therapy and veterinary applications. Accordingly, said subject may be a female animal such as a female mouse, rat, hamster, rabbit, guinea pig, ferret, cat, dog, chicken, sheep, bovine species, horse, camel, or primate. Preferably, the subject is a mammal (i.e. a female mammal). More preferably the subject is human (i.e. a female human). Most preferably, the subject is a postpartum female human. To analyze the amount of PAI-1, the subject is preferably from 1 day to 7 month after delivery. To analyze the activity of PAI-1, the subject is preferably from 2 weeks to 7 month after delivery.

The term "peripartum cardiomyopathy" or "PPCM" is commonly known in the art and relates to a form of dilated cardiomyopathy that is defined as a systolic left ventricular dysfunction occurring typically between the last month of pregnancy, under the delivery and in the months following delivery (Sliwa, 2010, Eur J Heart Fail. 12(8):767-78). As with other forms of dilated cardiomyopathy, PPCM involves systolic dysfunction of the heart with a decrease of the left ventricular ejection fraction (EF) with associated congestive heart failure and an increased risk of atrial and ventricular arrhythmias, thromboembolism (blockage of a blood vessel by a blood clot), and even sudden cardiac death. In essence, the heart muscle cannot contract forcefully enough to pump adequate amounts of blood for the needs of the body's vital organs. PPCM is a diagnosis of exclusion, wherein patients have no prior history of heart disease and there are no other known possible causes of heart failure. Echocardiogram is used to both diagnose and monitor the effectiveness of treatment for PPCM. The cause of PPCM is unknown. The process of PPCM begins with an unknown trigger that merges in a common path involving unbalanced oxidative stress, cleavage of the nursing hormone prolactin in the anti-angiogenic and proapoptotic 16K form. As the endothelium is the primary target the heart muscle subsequently faces insufficient oxygen and nutritian supply as well as a metabolic problem. This leads to decreased contractility but normally not to cardiomyocyte loss, a feature that explains the relatively high chance for recovery in most patients if they are diagnosed early and obtain optimal treatment (Hilfiker-Kleiner, 2007, Cell. 128: 589-600; Hilfiker-Kleiner, 2014, Nat Rev Cardiol. 11(6):364-70; Patten, 2012, Nature. 485(7398):333-8; Sliwa, 2010, Eur J Heart Fail. 12(8):767-78).

Herein, the terms "non-peripartum cardiomyopathy" or "non-peripartum CM" relate to every type of cardiomyopathy which is not a PPCM. For example, a non-peripartum cardiomyopathy may be a genetically inherited mutation in a cardiac gene (other than a mutation in the PAI-1 promoter), which under the stress of pregnancy is demasked and results in peripartum heart failure (Hilfiker-Kleiner, 2014, Nat Rev Cardiol. 11(6):364-70; Sliwa, 2010, Eur J Heart Fail. 12(8): 767-78).

The terms "plasminogen activator inhibitor-1" or "PAI-1" (sometimes also referred to as serpin E1) is known in the art. PAI-1 is an endogenous inhibitor of tissue-type plasminogen activator (tPA) and urokinase-type plasminogen activator (uPA), the activators of plasminogen and hence fibrinolysis. In the prior art, elevated levels of PAI-1 have been proposed as a marker for fibrinolytic and age-related disease progression (Ghosh, 2012, J Cell Physiol. 227(2):493-507). The nucleotide sequence of human PAI-1 mRNA is shown herein as SEQ ID NO: 1; the amino acid sequence of human PAI-1 is shown herein as SEQ ID NO: 2; and the nucleotide sequence of the human PAI-1 gene is shown herein as SEQ ID NO: 3. Herein, the terms "plasminogen activator inhibitor-1" or "PAI-1" also relate to a functional fragment of the PAI-1 polypeptide. A functional fragment of the PAI-1 polypeptide relates to a fragment of PAI-1 having a sufficient length to have PAI-1 activity, e.g. to have the ability to activate NF-kB. Such a functional fragment has at least 90%, preferably at least 95%, more preferably at least 98%, and even more preferably at least 99% of the length of the amino acid sequence which is shown herein as SEQ ID NO: 2. It is of note that the nucleic acid and amino acid sequences of PAI-1 given herein as SEQ ID NOs: 1 and 2, respectively are not limiting. Accordingly, the terms "plasminogen activator inhibitor-1" or "PAI-1" also encompasses PAI-1 polypeptides/nucleic acid molecules having amino acid or nucleic acid sequences being homologous to the amino acid or nucleotide sequences shown herein (i.e. in SEQ ID NOs: 1-3). In particular, the term terms "plasminogen activator inhibitor-1" or "PAI-1" also encompasses proteins having at least 90%, preferably at least 95%, more preferably at least 96%, even more preferably at least 97%, even more preferably at least 98% or even more preferably at least 99% identity with the amino acid sequence of SEQ ID NO: 2, and being functional, wherein the function comprises the ability to activate NF-kB (e.g. in endothelial cells). In addition, the term terms "plasminogen activator inhibitor-1" or "PAI-1" also encompasses proteins encoded by a nucleic acid sequence having at least 90%, preferably at least 95%, more preferably at least 96%, even more preferably at least 97%, even more preferably at least 98% or even more preferably at least 99% identity with the nucleic acid sequence as shown in SEQ ID NO: 1, and being functional, wherein the function comprises the ability to activate NF-kB (e.g. in endothelial cells). Preferably, herein the term "plasminogen activator inhibitor-1" or "PAI-1" relates to human PAI-1. The mRNA sequence and the amino acid sequence of human PAI-1 are shown herein as SEQ ID NOs: 1 and 2, respectively. However, the herein provided means and methods may also be useful for veterinary use. Therefore, the term "plasminogen activator inhibitor-1" or "PAI-1" also encompasses the PAI-1 protein of other organisms such as mouse, rat, hamster, rabbit, guinea pig, ferret, cat, dog, chicken, sheep, bovine species, horse, camel, or primate. However, most preferably, the terms "plasminogen activator inhibitor-1" or "PAI-1" relate to a protein having the amino acid sequence as shown in SEQ ID NO: 2 or being encoded by the nucleotide sequence as shown in SEQ ID NO: 1.

The term "activity" (also designated as "functionality") defines whether a polypeptide (preferably PAI-1) is functional. A polypeptide is "functional" means, in context of the invention, that the polypeptide has the ability to carry out a specific "function". Accordingly, the terms "activity" or "functionality" relate to the ability of a specific protein to carry out a specific function. For instance, in context of the present invention, a function of PAI-1 comprises the ability to activate NF-kB (e.g. in endothelial cells). The measurement of the activity (i.e. the functionality) of PAI-1 is described herein above.

The term "inhibitor" is known in the art and relates to a compound/substance capable of fully or partially preventing or reducing the physiologic function (i.e. the activity) of (a) specific protein(s) (e.g. of PAI-1). Inhibitors are also known as "antagonists". In the context of the present invention, the inhibitor of PAI-1 may prevent or reduce or inhibit or inactivate the physiological activity of PAI-1 (i.e. the activation of NF-kB), e.g., upon binding of said compound/substance to PAI-1. Binding of an inhibitor/antagonist to PAI-1 may prevent the binding of an endogenous activating molecule (e.g. 16K prolactin) to PAI-1, and thereby inhibiting the activity of PAI-1. In the context of the present invention, an "inhibitor" of PAI-1 may be capable of preventing the function of PAI-1 by preventing or reducing the expression of the PAI-1 gene (e.g. the gene having the nucleic acid sequence as shown in SEQ ID NO: 3). Thus, an inhibitor of PAI-1 may lead to a decreased expression level of PAI-1 (e.g. decreased level of PAI-1 mRNA or PAI-1 protein) which is reflected in a decreased functionality (i.e. activity) of PAI-1, wherein the function of PAI-1 comprises the ability to activate NF-kB (e.g. in endothelial cells). This decreased functionality can be measured, for example, by the herein described method to assay PAI-1 activity. An inhibitor of PAI-1, in the context of the present invention, accordingly, may also encompass transcriptional repressors of PAI-1 expression that are capable of reducing the level of PAI-1. As used herein, a specific inhibitor of PAI-1 targets the PAI-1 polypeptide or a functional fragment thereof and/or the nucleic acid molecule encoding PAI-1 or a functional fragment thereof. Accordingly, all means and methods which result in a decrease in activity (which may be reflected in a lower expression of PAI-1), are to be used as PAI-1 inhibitors in accordance with the present invention.

As described above, the present invention relates to an inhibitor of PAI-1 for use in the treatment of PPCM, wherein said inhibitor is an interference molecule, which is directed against the mRNA of the plasminogen activator inhibitor-1. Among these molecules, it is preferred in context of the present invention that the inhibitor of PAI-1 is a siRNA molecule. However, in context of the present invention the most preferred PAI-1 inhibitor is PAI-039.

The term "RNA interference molecule" as used herein refers to a short (usually <30 nucleotides), mostly double-stranded RNA molecule which induces sequence-specific degradation of homologous single-stranded RNA. For example, RNA interference molecules can induce the degradation of a defined messenger RNA (mRNA) (e.g. the mRNA of PAI-1). Herein the term "RNA interference molecule" also comprises chemically modified RNA nucleotides, e.g. locked nucleic acids (LNA). Using RNA interference molecules for the degradation of RNA is a very powerful technique to down regulate or obviate (i.e. "knock-down") the expression of specific genes (e.g. of the PAI-1 gene). For example, RNA interference can be induced through transfection or microinjection of RNA interference molecules. Preferably, the RNA interference molecule is a small interfering RNA (siRNA) which is a RNA molecule with a length of <30 nucleotides, preferably of 19 to 23 nucleotides. However, in accordance with the present invention, also hairpin or duplex siRNAs may be used as PAI-1 inhibitor. Using siRNAs which are directed against the PAI-1 mRNA for treating PPCM has the advantage that the expression of PAI-1 can be inhibited in a cell type-specific manner. However, since PPCM starts as a systemic disease in the blood vessel that damages not only the heart but also other organs it is envisaged to target PAI-1 systemically, i.e. everywhere. SiRNAs built the sequence specific part of an RNA-induced silencing complex (RISC), a multicomplex nuclease that destroys messenger RNAs homologous to the silencing trigger. Elbashir; 2001; EMBO J; 20; 6877-6888 showed that duplexes of 21 nucleotide RNAs may be used in cell culture to interfere with gene expression in mammalian cells. In mammalian cells, the interference activity of siRNA molecules is usually transient, lasting for only 3 to 5 days. Thus, by using siRNA molecules in postpartum women, PAI-1 can be specifically down regulated for a defined period of time. Since women with PPCM usually recover during the first year after onset of the disease, the administration of siRNA or the PAI-1 pharmacological inhibitor (and the down regulation of the PAI-1 expression) is preferably stopped after a defined amount of time. For example blocking prolactin seems to be sufficient for about eight weeks while beta-blockers and ACE-inhibitors are normally given for at least one year. The administration of PAI-1 inhibitors may be similar as the prolactin blockade, i.e. around two months. However, whether the PAI-1 expression can also be down regulated or obviated over longer durations; e.g. by using siRNA expression plasmids in the context of mutated PAI-1 will be analyzed in clinical studies. Therefore, the PAI-1 expression may also be constitutively down regulated. Stable expression of siRNAs in mammalian cells is inter alia shown in Brummelkamp, 2002, Science, 296: 550-553. Also Paul, 2002, Nat Biotechnol, 20: 505-508 documented the effective expression of siRNA in human cells. RNA interference by expression of siRNAs and hairpin RNAs in mammalian cells was also shown by Yu, 2002, PNAS, 99: 6047-6052.

Methods to deduce and construct RNA interference molecule (particularly siRNAs and/or shRNAs) are known in the art and are described, e.g., in Elbashir, 2002, Methods, 26: 199-213, at the internet web sites of commercial vendors of siRNA, e.g. Qiagen GmbH (quiagen.com); GE Healthcare (dharmacon.gelifesciences.com); and Ambion (lifetechnologies.com), Biosprings or Darmacon. In addition, software tools are available online to deduce siRNAs from a given mRNA sequence. Uridine residues in the 2-nt 3' overhang can be replaced by 2'deoxythymidine without loss of activity, which significantly reduces costs of RNA synthesis and may also enhance resistance of siRNA duplexes when applied to mammalian cells (Elbashir, 2001, loc. cit). The siRNAs may also be synthesized enzymatically using T7 or other RNA polymerases (Donze, 2002, Nucleic Acids Res, 30: e46). Short RNA duplexes that mediate effective RNA interference (esiRNA) may also be produced by hydrolysis with *Escherichia coli* RNaseIII (Yang; 2002; PNAS, 99: 9942-9947). Furthermore, expression vectors have been developed to express double stranded siRNAs connected by small hairpin RNA loops in eukaryotic cells (e.g. Brummelkamp, 2002, Science, 296: 550-553). All of these constructs may be developed with the help of the programs named above. In addition, commercially available sequence prediction tools incorporated in sequence analysis programs or sold separately, e.g. the siRNA Design Tool offered by oligoEngine.com (Seattle, Wash.) may be used for siRNA sequence prediction. For example, by knowing the mRNA sequence of PAI-1 (e.g. the sequence of PAI-1 as shown in SEQ ID NO: 1), the person skilled in the art can easily obtain siRNA molecules for the inhibition (i.e. down regulation or obviation) or PAI-1 expression. siRNAs which specifically target a defined RNA are commercially available, e.g. from Biosprings and Darmacon. siRNAs which effectively down regulate the expression of PAI-1 are provided by Santa Cruz Biotechnology (Catalog # SC-36179) or by Ddharmacon, SMARTpool: ON-TARGETplus SERPINE1 siRNA (Catalog # L-019376-01-0005).

The present invention also relates to an inhibitor of PAI-1 for use in the treatment of PPCM, wherein said inhibitor is an antibody which specifically binds to PAI-1. Preferably, said antibody is an antagonistic antibody. As used herein, the term "antagonistic antibody" describes an antibody that is capable of inhibiting and/or neutralizing the (biological) activity of a specific target protein, such as PAI-1. For instance, an antagonistic antibody may block the binding or substantially reduce the binding of PAI-1 to other molecules, such as to 16K prolactin and thereby inhibiting the function of PAI-1 i.e., the ability to activate NF-kB. This decreased functionality can be measured, for example, by measuring the activity of NF-kB as described herein. It is envisaged that the antibody (e.g. the antagonistic antibody) preferably and specifically binds PAI-1 or fragments thereof. Methods for the use and production of (antagonistic) antibodies are well known in the art and are described, e.g., in Tartaglia, 1992, J Biol Chem, 267: 4304-4307; Tartaglia, 1993, Cell, 73: 213-216 and WO 94/09137. Antagonistic antibodies that target PAI-1 may also be produced, for example, by performing screening techniques using a human Fab phagemid library (see, inter alia, Huag, 2006, J Leuko Biol, 80: 905-914 and Hoet, 2005, 23: 344-348). In addition, the production of antagonistic antibodies by phage display is described in Molek, 2011, Molecules, 16: 857-887. The functionality of an antagonistic antibody, i.e. the ability of an antibody to act antagonistic, can be assayed as described in the art. Possible methods to assay the functionality of an antagonistic antibody comprise, for example, phage ELISA, cell binding assays and blocking assays as described in, for example, Huag, 2006, J Leuko Biol, 80: 905-914; Hoet, 2005, 23: 344-348; Jostock, 2004, 289: 65-80; and Baumann, 2010, J Exp Med, 207: 2689-701.

Herein the term "antibody" is used in the broadest sense and specifically encompasses intact monoclonal antibodies, polyclonal antibodies, multispecific antibodies (e.g., bispecific antibodies) formed from at least two intact antibodies, and antibody fragments, so long as they exhibit the desired biological activity (i.e. specifically binding to PAI-1). Also human, humanized, camelized or CDR-grafted antibodies are comprised.

The term "monoclonal antibody" as used herein refers to an antibody obtained from a population of substantially homogeneous antibodies, i.e. the individual antibodies of the population of antibodies are identical except for possible naturally occurring mutations that may be present in minor amounts. Monoclonal antibodies are highly specific, being directed against a single antigenic site. Furthermore, in contrast to polyclonal antibody preparations which include different antibodies directed against different determinants (epitopes), each monoclonal antibody is directed against a single determinant on the antigen. In addition to their specificity, the monoclonal antibodies are advantageous in that they may be synthesized uncontaminated by other antibodies. The modifier "monoclonal" indicates the character of the antibody as being obtained from a substantially homogeneous population of antibodies, and is not to be constructed as requiring production of the antibody by any particular method. For example, the monoclonal antibodies which are comprised in the sample of the methods of the present invention may be made by the hybridoma method first described by Kohler, Nature 256 (1975) 495, or may be made by recombinant DNA methods (see, e.g., U.S. Pat. No. 4,816,567).

"Antibody fragments" comprise a portion of an intact antibody. The term "antibody fragments" includes antigen-binding portions, i.e., "antigen binding sites" (e.g., fragments, subsequences, complementarity determining regions (CDRs)) that retain capacity to bind an antigen (such as CD20, VEGF of Her3), comprising or alternatively consisting of, for example, (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward; 1989; Nature 341; 544-546), which consists of a VH domain; and (vi) an isolated complementarity determining region (CDR). Antibody fragments or derivatives further comprise F(ab')2, Fv or scFv fragments or single chain antibodies.

The phrase "specifically bind(s)" or "bind(s) specifically" when referring to a binding molecule refers to a binding molecule (e.g. an antibody) which has intermediate or high binding affinity, exclusively or predominately, to a target molecule, preferably PAI-1. The phrase "specifically binds to" refers to a binding reaction which is determinative of the presence of a target (preferably the PAI-1 protein, a nucleic acid molecule encoding the PAI-1 protein, or the PAI-1/16K prolactin complex) in the presence of a heterogeneous population of proteins and other biologics. Thus, under designated assay conditions, the specified binding molecules bind preferentially to a particular target (preferably the PAI-1 protein, a nucleic acid molecule encoding the PAI-1 protein, or the PAI-1/16K prolactin complex) and do not bind in a significant amount to other components present in a test sample. Specific binding to a target protein under such conditions may require a binding molecule that is selected for its specificity for a particular target protein. A variety of assay formats may be used to select binding molecules that are specifically reactive with a particular target protein. For example, solid-phase ELISA immunoassays, immunoprecipitation, Biacore and Western blot may be used to identify binding molecules that specifically react with the PAI-1 protein or the PAI-1/16K prolactin complex. The PAI-1 protein or the PAI-1 protein which is comprised in the PAI-1/16K prolactin complex is most preferably a polypeptide which has the amino acid sequence as shown in SEQ ID NO: 2. However, the PAI-1 protein may also be a polypeptide having at least 90%, preferably at least 95%, more preferably at least 96%, even more preferably 97%, even more preferably at least 98% or even more preferably at least 99% identity with the amino acid sequence of SEQ ID NO: 2, and being functional, wherein the function is the ability to activate NF-kB (e.g. in endothelial cells). To assay whether a binding molecule specifically binds to a particular nucleic acid molecule (e.g. a nucleic acid molecule encoding the PAI-1 protein) the following methods can be used (immunoprecipitation, IP). The nucleic acid molecule encoding the PAI-1 protein is most preferably a nucleic acid molecule which has the nucleic acid sequence as shown in SEQ ID NO: 1. However, the nucleic acid molecule encoding the PAI-1 protein may also be a nucleic acid molecule having at least 90%, preferably at least 95%, more preferably at least 96%, even more preferably 97%, even more preferably at least 98% or even more preferably at least 99% identity with the nucleic acid sequence of, SEQ ID NO: 1, and being functional, wherein the function is the ability to activate NF-kB (e.g. in endothelial cells). Typically, a specific or selective reaction will be at least twice background signal or noise and more typically more than 10 times background. Or, in other words, the phrase "specifically binds to" refers to a binding reaction that is determinative of the presence of the target protein (preferably PAI-1) in a heterogeneous population of proteins and other biologics. Typically, an antibody which specifically binds to a certain target (preferably PAI-1) binds to said target with an association constant ($K_a$) of at least about $1\times10^6$ $M^{-1}$ or $10^7$ $M^{-1}$, or preferably about $10^8$ $M^{-1}$ to $10^9$ $M^{-1}$, or more preferably about $10^{10}$ $M^{-1}$ to $10^{11}$ $M^{-1}$ or higher. Moreover, an binding molecule (e.g. an antibody) that specifically binds to a particular target (preferably PAI-1) preferably binds to this target with an affinity that is at least two-fold greater than its affinity for binding to a non-specific target (e.g., BSA, casein) other than the predetermined target or a closely-related target.

As described above, the invention also relates to an inhibitor of PAI-1 for use in the treatment of PPCM, wherein said inhibitor is PAI-039, as defined above.

In context of the present invention, "homologous" or "percent homology" means that amino acid or nucleotide sequences have identities of at least 90%, 95%, 96%, 97%, 98% or 99% to the sequences shown herein, e.g. those of SEQ ID NO: 1, 2, or 3, wherein the higher identity values are preferred upon the lower ones. In accordance with the present invention, the term "identity/identities" or "percent identity/identities" in the context of two or more nucleic acid or amino acid sequences, refers to two or more sequences that are the same, or that have a specified percentage of amino acid residues or nucleotides that are the same (e.g., at least 90%, preferably at least 95%, more preferably at least 96%, even more preferably 97%, even more preferably at least 98% or even more preferably at least 99% identity with the nucleic acid sequences of, e.g., SEQ ID NO: 1, or 3, or with the amino acid sequences of, e.g., SEQ ID NO: 2, and being functional, wherein the function comprises the ability to activate NF-kB, [e.g. in endothelial cells]), when compared and aligned for maximum correspondence over a window of comparison, or over a designated region as measured using a sequence comparison algorithm as known in the art, or by manual alignment and visual inspection.

Preferably the described identity exists over a region that is at least about 300 amino acids, preferably at least 350 amino acids, more preferably at least 400 amino acids, and most preferably all amino acids in length. In case of nucleotide sequences, the described identity most preferably exists over a region that is at least 1,000, preferably at least 2,000, or more preferably at least 3,000 and most preferably all nucleotides in length.

Those having skills in the art will know how to determine percent identity between/among sequences using, for example, algorithms such as those based on CLUSTALW computer program (Thompson, 1994, Nucl Acids Res, 2: 4673-4680) or FASTDB (Brutlag, 1990, Comp App Biosci, 6: 237-245), as known in the art. Also available to those having skills in this art are the BLAST and BLAST 2.0 algorithms (Altschul, 1997, Nucl Acids Res 25: 3389-3402; Altschul, 1993, J Mol Evol, 36: 290-300; Altschul, 1990, J Mol Biol 215: 403-410). For example, BLAST 2.0, which stands for Basic Local Alignment Search Tool BLAST (Altschul, 1997, loc. cit.; Altschul, 1993, loc. cit.; Altschul, 1990, loc. cit.), can be used to search for local sequence alignments. BLAST, as discussed above, produces alignments of both nucleotide and amino acid sequences to determine sequence similarity. Because of the local nature of the alignments, BLAST is especially useful in determining exact matches or in identifying similar sequences. Analogous computer techniques using BLAST (Altschul, 1997, loc. cit.; Altschul, 1993, loc. cit.; Altschul, 1990, loc. cit.) are used to search for identical or related molecules in nucleotide databases such as GenBank or EMBL.

The present invention is further described by reference to the following non-limiting Tabels, Figures and Examples.

The Table 1 provides the clinical information on the patient collectives and the controls The Figures show:

FIG. 1: Serum and plasma PAI-1 levels in healthy postpartum women and in patients with PPCM. (A) Kinetics of PAI-1 in plasma of non-pregnant controls (NP), healthy pregnant women (20.-34. week of pregnancy: Prg), healthy prepartal women (1-4 d before delivery: pre-del), early-PP (1-3 day postpartal), late-PP (2 weeks till 10 month after delivery) and (B) in serum of early-PP and late-PP. PAI-1 levels in (C) plasma and (D) serum of PPCM patients (serum: n=22, plasma: n=39), healthy postpartal controls (serum: n=23, plasma: n=29) and patients with DCM (serum: n=15). **$P<0.01$ vs. PPCM, all data are mean±SD.

FIG. 2: Follow up analyses of PAI-1 in PPCM patients. (A) Plasma PAI-1 levels of PPCM patients baseline and 6 months after diagnosis (n=17). (B) LVEF of the same PPCM patients at baseline and 6 months after diagnosis (n=17). (C) PAI-1 levels in serum of three PPCM patients after delivery of a subsequent pregnancy compared to healthy postpartum controls (early- and late-PP, n=20). (D) LVEF of the same three patients at index PPCM and after delivery of subsequent PPCM. **$P<0.01$ vs. early- and late-PP, all data are mean±SD.

FIG. 3: NF-kB activation measured by a luciferase reporter plasmid in rat heart endothelial cells (RHE-A cells) exposed with serum of PPCM women and healthy postpartal control women. (A) Relative luciferase activity indicating NF-kB activity of healthy postpartum controls, early-PP (n=4) and late-PP (n=6) after delivery, one patient 7 weeks postpartum was set at 100%. (B) NF-kB activity induced by serum from PPCM patients at the time of diagnosis (2 weeks—5 month postpartum, n=9) compared with serum from late-PP (n=6, mean was set at 100%). (C) NF-kB induced luciferase activity in control RHE-A and in RHE-A with uPAR knockdown treated with serum from PPCM patients (n=3) or postpartum controls (n=4, mean was set at 100%). (D) NF-kB activity measured in serum of two PPCM patients incubated with the PAI-1 inhibitor tiplaxtinin (PAI-039, 1 mM) for 1 h at room temperature prior admission to RHE-A cells compared to RHE-A cells treated with serum alone from the same patients (mean was set at 100%). Luciferase activity was measured 3 h after addition of sera in 2-3 biological and 2 technical replicates. (**$P<0.01$, *$P<0.05$ vs. PPCM). All data are mean±SD.

Figure 4:
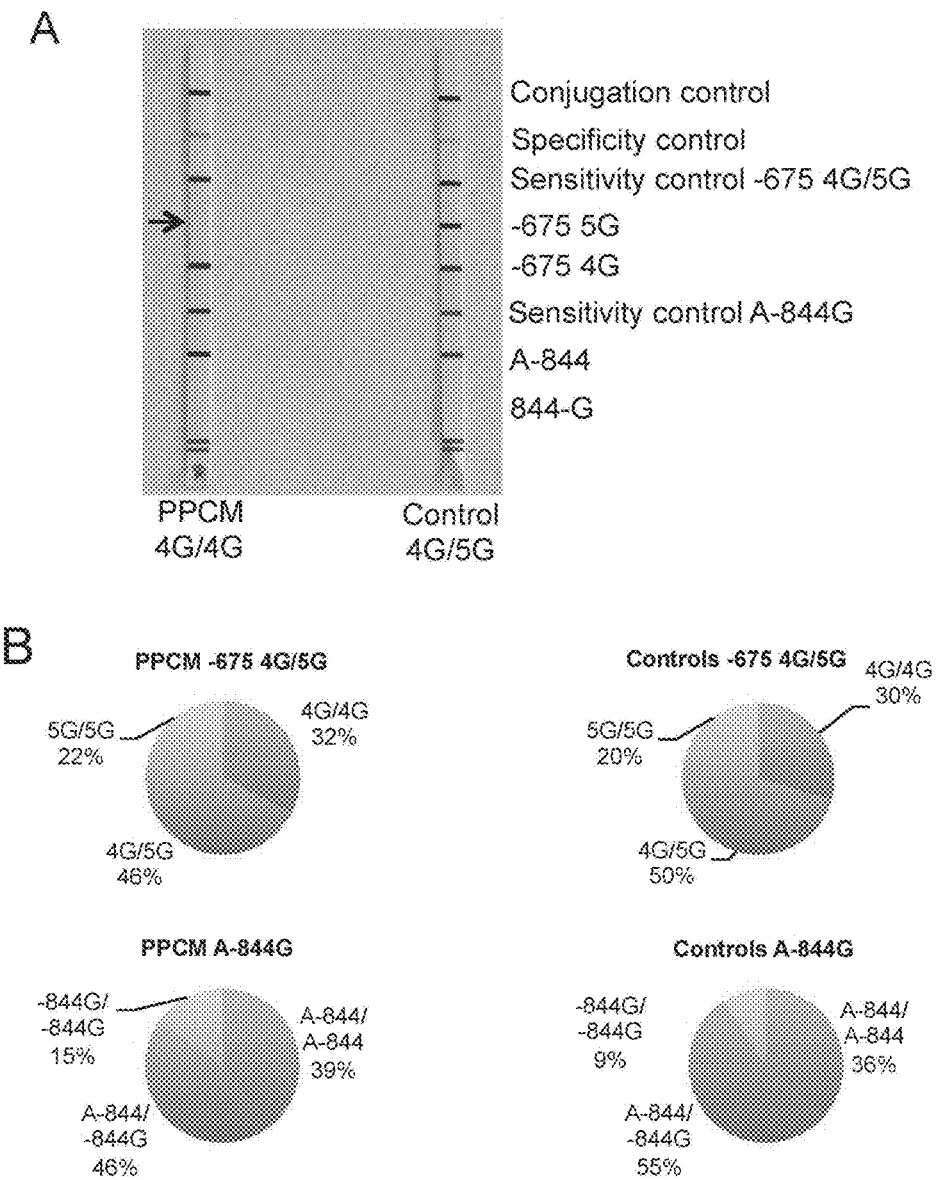

FIG. 4: Analyses of PAI-1 gene polymorphisms in PPCM patients. (A) The common polymorphisms at position −675 and −844 of the PAI-1 promoter were analyzed using the test kit for PAI-1 polymorphism from Hain Life Science GmbH. (B) Distribution of the polymorphisms shown in (A) in patients with PPCM (n=46) as compared to healthy post-partum control women (n=44). (C) Novel polymorphism at position −747 in the PAI-1 promoter (SEQ ID NO: 4) from clones #1-5 (SEQ ID NOs: 5-9) from a PPCM patient with high PAI-1 blood levels after index PPCM and after subsequent delivery and (D) time course of PAI-1 plasma levels in correlation with left ventricular function (ejection fraction, % LVEF) in the same PPCM patient at first diagnosis and in a subsequent pregnancy and delivery with immediate treatment to prevent further heart failure).

FIG. 5: A) Chemical structure of PAI-039. (B) Chemical structure of bromocriptine.

Figure 6:
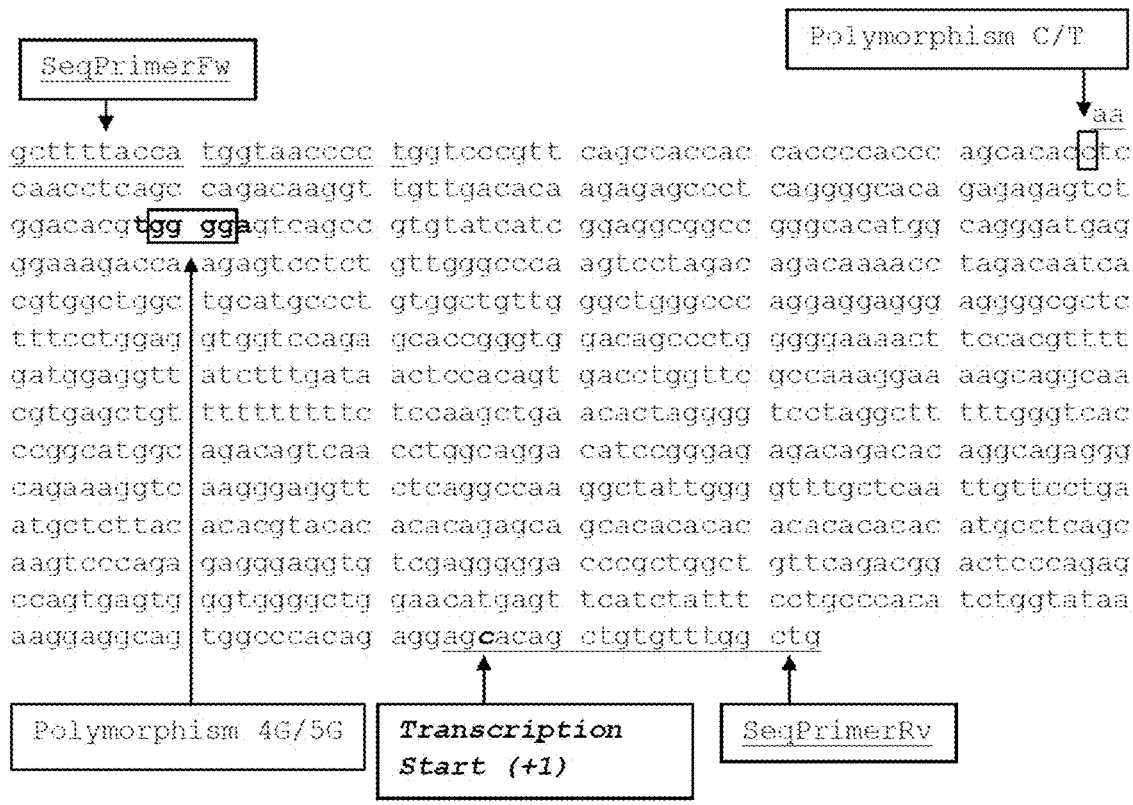

FIG. 6: PAI-1 promoter. The genomic sequence of the PAI-1 promoter (SEQ ID NO:10) is shown. The positions of the polymorphisms 4G/5G and C/T are indicated by rectangles. The forward (SeqPrimerFw) and reverse (SeqPrimerRv) primers for sequencing are underlined. The transcription start (+1) is indicated by italc type and bold face.

EXAMPLE 1

Plasminogen Activator Inhibitor-1 is a Novel Biomarker and Therapeutic Target for Peripartum Cardiomyopathy Summary of the Example PAI-1 serum and plasma levels were measured by ELISA in patients with acute PPCM (at diagnosis and at 6 months follow up), healthy non-pregnant controls (NP), healthy women during pregnancy (Prg), immediately before delivery (Pre-Del), in the first postpartum week (Early-PP) and 2 weeks to 10 months postpartum (Late-PP). Cardiac function in Early-PP and Late-PP was normal with LVEF>55% and impaired in PPCM (<45% in all patients with an average LVEF of 25±9% at diagnosis). A small collective of patients with dilated cardiomyopathy (DCM, LVEF: 32±9%) was used for testing disease specificity of PAI-1. In Early-PP and Late-PP, PAI-1 levels were comparable to NP controls. In contrast, PAI-1 levels were elevated in the majority of PPCM patients independent of the time of diagnosis, while they were with normal range in DCM patients and in two patients with classical genetic forms of peripartum heart failure. Recovery from PPCM after 6 months was associated with a decrease in PAI-1 levels. Patients with a high risk for PPCM due to PPCM in a previous pregnancy, displayed elevated PAI-1 levels after delivery even before onset of cardiac dysfunction. PPCM patients displayed also significantly higher PAI-1/uPAR-mediated NF-kB activation as analyzed by a luciferase reporter assay in rat heart endothelial cells compared to Late-PP controls. Common PAI-1 gene polymorphisms (−675 4G/4G or −844 5G/5G) displayed a similar incidence in PPCM patients and in healthy postpartum controls. However, a new polymorphism, a point mutation (C to T) at −747 was discovered in a PPCM patient with continuous high PAI-1 levels. These data show that PAI-1 appears to be a promising biomarker candidate with robustly elevated serum levels in PPCM patients compared to healthy PP women independent of the time of diagnosis in relation to delivery. It may as well distinguish PPCM from other forms of heart failure. Activity assays analyzing specifically the PAI-1 mediated NF-kB activation are possible and can be used to further identify the presence of PPCM specific pathomechanisms. Finally, since pharmacological inhibition of PAI-1 or the uPAR interrupted NF-kB activation, targeting the PAI-1/uPAR system may be a novel therapeutic option to treat PPCM.

Materials and Methods

Cell culture media were obtained from Biochrome. All other chemicals were purchased from Sigma-Aldrich.

Patients

The local ethics committee of Hannover Medical School approved this study. All patients provided written informed consent. All 45 patients enrolled were diagnosed with PPCM according to the position statement from the Heart Failure Association of the European Society of Cardiology Working Group on peripartum cardiomyopathy (Sliwa, 2010, Eur J Heart Fail 12:767-778). A collective of patients with heart failure due to dilated cardiomyopathy (DCM, n=15) was used for comparison with other forms of heart failure. The control collective consisted of healthy postpartum women with no echocardiographic abnormalities of cardiac structure or function (LVEF>55%, n=27), healthy pregnant women (n=7) and healthy non-pregnant women (n=8).

Blood Tests

Blood samples were collected in S-Monovette® tubes containing ethylenediaminetetraacetic acid (EDTA, for plasma) or clot activator (for serum) at the time point of first diagnosis (baseline) and at the follow-up visit (6 months after diagnosis) in PPCM patients and from peripartum healthy controls and age-matched non pregnant women. Laboratory workup was performed as routine investigation by hospital laboratories for N-terminal pro-brain natriuretic peptide (NTproBNP). For analyses of PAI-1, plasma or serum were separated by centrifugation at 1500 rpm for 10 min and aliquots were stored at −80° C. PAI-1 was measured using the Quantikine ELISA human total serpine E1/PAI-1 Immunoassay from R&D systems [catalogue number DTSE100] strictly according to the manufacturer's protocol.

In brief, to generate the required dilutions (25-fold dilution for serum samples and 10-fold dilution for plasma samples), 20 µl of the serum sample was added to 480 µl of Calibrator Diluent RD5-26 Concentrate and 50 µl of the plasma sample was added to 450 µl of Calibrator Diluent RD5-26 Concentrate, respectively. Subsequently, samples were added to the wells as duplicates and several incubation and washing steps were done according to the manufacturer's protocol. Four minutes after final addition of the Stop Solution the optical density of each well was determined at 450 nm and 570 nm using a microplate reader [Varioskan Flash Top/Bottom, Thermo Scientific, catalogue number: 5250040]. The readings at 570 nm were substracted from those at 450 nm for correction, duplicate readings were averaged and the average zero standard optical density was substracted, respectively. A standard curve was created by generating a four parameter logistic curve-fit using GraphPad Prism. Determined concentrations finally were multiplied by the dilution factor regarding the dilution described above. Samples from two patients were repeatedly analyzed in each measurement to control inter-assay precision.

PAI-1/16K Prolactin Activity Assay

The PAI-1/uPAR-mediated NF-kB activity was determined in the rat heart endothelial cell line RHE-A. In detail, RHE-A cells stably expressing the NFκB-promoter sequence upstream from Gaussia luciferase reporter (lentiviral NF-kB luciferase reporter construct) were used to analyse the NFκB-activation of sera obtained from PPCM patients and healthy controls. To specifically determine the involvement of PAI-1/16K prolactin/tPa/uPA/uPAR in NFkB activation, RHE-A cells expressing the NF-kB reporter construct were subjected for uPAR knockdown by lentiviral siRNA against uPAR or control lentiviral siRNA. In order to inhibit PAI-1 activity, the inhibitor PAI-039 which is also known as tiplaxtinin (CAS Registry Number: 393105-53-8) was used. Tiplaxtinin was used at 1 mM final assay concentration in the presence of 10% DMSO and was preincubated with patient sera for 1 h at room temperature. DMSO treated sera served as controls. RHE-A cells were routinely cultivated in a T75 flask using Dulbecco's Modified Eagle Medium (DMEM) supplemented with 10% fetal bovine serum and 1% penicillin/streptomycin. For NF-κB-activity assay, $4 \times 10^4$ cells per well were seeded in a 96-well microplate (Thermo Scientific, USA) and grown for 1 day in FBS-supplemented medium until confluence. After 2 washes, 200 µl serum-free DMEM were added and cells were cultivated overnight. The cell culture supernatant of the overnight culture was then stored away at −80° C. for calibration. Following removal of medium, 15% serum from PPCM patients or healthy controls in DMEM were added to the cells in a total volume of 200 µl. All samples including patient sera were prepared as duplicates. After 3 h incubation, supernatants were removed and directly subjected for luminometry. For luminometric measures, BioLux® Gaussia Luciferase Assay Kit (New England BioLabs, Germany) was used. 20 µl from each sample was transferred to a white polystyrene microplate (Thermo Scientific, USA) in triplicates. After preparation of GLuc assay solution for the respective number of samples (e.g. 50 µl substrate added to 5 ml of assay buffer), an injector-equipped microplate reader (Varioskan™ Flash Multimode Reader, Thermo Scientific, USA) was used to inject 50 µl of assay solution into each well. Luminometric measures were integrated for 5 sec after an initial lag phase of 5 sec. Serum-free medium incubated for 3 h on RHE-A cells and unconditioned medium served as technical controls.

Analyses of Genetic Polymorphisms in the PAI-1 Promoter

The PAI-1 polymorphisms −675 5G/5G, −675 4G/4G, −675 4G/5G, −844G/-844G, A-844/A-844 and A-844/-844G were analyzed from total genomic DNA using a GenoType PAI-1 assay (Hain Lifescience, version 2.0, catalogue number: 22296) strictly according to the manufacturer's protocol.

Total genomic DNA from PPCM patients and healthy postpartum controls was isolated either using the Genocard (Hain Lifescience, catalogue number: G001) or buffy coat or full blood. For isolation with the Genocard, 15 µl of blood was spotted on the card and cut out for direct PCR amplification with the GenoType PAI-1 assay according to the manufacturer's protocol.

DNA was isolated from 100 µl whole blood or 100 µl buffy coat using the DNeasy Blood & Tissue Kit (Qiagen, catalogue number: 69504) according to the manufacturer's protocol.

For identification of additional PAI-1 promoter polymorphisms, the PAI-1 promoter region extending from −806 to +19 was amplified from genomic DNA of three PPCM patient with specifically high (>71 ng/ml) and three postpartum controls with low (<18 ng/ml) PAI-1 plasma levels by PCR using the following primers: forward primer: 5'-AAGCTTTTACCATGGTAACCCCT-3', reverse: 5'-GCAGCCAAACACAGCTGTGCT-3' (Fink, 2002, Blood 99:2077-2083). The resulting 826 bp products were subcloned in the pGEM®-T Easy Vector using the pGEM®-T Easy Vector System I (Promega, A3600) in accordance to the manufacturers instructions. Shortly, 2 µl of the respective PCR products and 1 µl of vector were used and ligation was performed overnight at 4° C. XL1-Blue competent cells were transformed with the resulting PAI-1 promoter containing vectors and positive clones were selected by amplicillin resistance and blue-white screening. Plasmid DNA of 8 distinct clones of each induvidual were amplified by culture in ampicillin-containing LB medium overnight at 37° C. Plasmid DNA was isolated by use of the QIAprep Spin Miniprep Kit (Qiagen, #27106) as indicated by the manufacturer and DNA was eluted in sterile water. All clones were screened by PCR using the primer pair indicated above to validate the presence of the PAI-1 promoter sequence. At least five clones of each respective individuum containing the PAI-1 promoter region were subsequently sequenced by use of the T7 primer 5'-TAATACGACTCAC-TATAGGG-3' (Eurofins). Sequence data files were converted using the EMBOSS Secret program and multiple sequence alignments were performed using the Clustal-Omega program.

Statistical Analyses

Data are presented as mean±SD. Differences between groups were analyzed by Student's t test or ANOVA, followed by Bonferroni as appropriate. A two-tailed P value of <0.05 was considered statistically significant.

Results

Clinical Data of PPCM and DCM Patients and Postpartum Controls

Clinical data of patients diagnosed with PPCM are provided in Table 1. Onset of disease in PPCM patients occurred in the first week after delivery till 8 months postpartum. Left ventricular ejection fraction (LVEF) and some clinical data were also available for postpartum controls and for DCM patients (Table 1).

Time Course Analysis of PAI-1 in Serum and Plasma

In order to evaluate the pregnancy-related kinetics of PAI-1, levels of PAI-1 have been analyzed in plasma of non-pregnant controls, healthy pregnant and in healthy postpartum women (in the first week after delivery: early-PP and 2 weeks till 10 month after delivery: late-PP). As shown in FIG. 1A, except for a marked increase immediately prior delivery, mean PAI-1 levels did not differ significantly between all other time points pre- and postpartum but tended to be slightly higher compared to non-pregnant controls. Low and stable PAI-1 levels were also present in serum probes of early- and late-PP women (FIG. 1B).

PAI-1 Serum and Plasma Levels are Elevated in Patients with PPCM but not in Patients with Dilated Cardiomyopathy Next we measured serum and plasma PAI-1 levels in patients with acute onset of PPCM. As shown in FIG. 1C and D, plasma and serum PAI-1 levels were elevated in the majority of PPCM patients compared to healthy postpartum controls and to non-pregnant controls. In contrast, serum PAI-1 levels in DCM patients did not differ significantly from healthy postpartum controls (FIG. 1D).

In Contrast to PPCM Patients, PAI-1 Levels Appeared Normal in Patients with Peripartum Heart Failure Due to Underlying Genetic Cardiomyopathy We previously showed that about 16% of patients with diagnosed PPCM display a positive family history of cardiomyopathy including dilated cardiomyopathy (DCM) and sudden cardiac death (Haghikia, 2013, Basic Res Cardiol 108:366). As these patients face a higher risk for adverse outcome, an optimal feature of a biomarker for PPCM would be to distinguish between "true" PPCM and genetic forms of heart failure triggered by pregnancy stress. Interestingly, two patients with peripartum heart failure and known cardiomyopathy causing mutations (one in titin and one in laminin) display serum levels of PAI-1 within the range of healthy postpartum controls (PAI-1 serum levels in patient with titin mutation: 80.66 ng/ml, in patient with laminin mutation: 87.79 ng/ml compared to the mean of postpartum control: 61.25±18.47 ng/ml, n=23). For comparison the mean of all PPCM patients was 157±64.19 ng/ml (n=22).

PAI-1 Levels in Patients with PPCM Decrease Under Medical Therapy

All PPCM patients in the present collective were treated with standard medication for heart failure (Table 1). Follow up analyses after 6 months in a subgroup of patients who were all treated with beta-blockers and ACE-inhibitors or ARB and with Bromocriptine (1 week to 6 weeks) showed a decrease in plasma PAI-1 in the majority of patients whereas cardiac function increased (FIGS. 2A and B).

Elevated Serum PAI-1 Levels in Patients with a High Risk for PPCM Due to a PPCM in a Previous Pregnancy In order to evaluate if PAI-1 levels may also serve as a marker indicating the risk for PPCM, we analyzed PAI-1 levels in serum of three PPCM patients who improved their cardiac function and got pregnant again. PAI-1 serum levels were measured within the first week after delivery and compared to healthy postpartum controls within the same time frame. As shown in FIG. 3C, PAI-1 serum levels were significantly higher after delivery of a subsequent pregnancy in all three PPCM patients compared to healthy postpartum controls. Because of their high risk for relapse, all three PPCM patients were treated with heart failure medication (beta-blocker, ACE-inhibitors), Bromocriptine and anti-coagulation therapy as soon as possible after delivery. This treatment was associated with maintained cardiac function and no relapse of the disease (FIG. 3D).

Serum of PPCM Patients Increases NF-kB Activation Via PAI-1 and the uPAR Receptor in Endothelial Cells It has recently been shown that PAI-1 specifically in complex with 16K prolactin, tPA/uPA and uPAR induces activity of nuclear factor 'kappa-light-chain-enhancer' of activated B-cells (NF-kB) (Bajou, 2014, Nat Med 20:741-747). To analyze whether NF-kB activation was mediated by uPAR signaling we used RHE-A cells stably transfected with a NF-kB driven luciferase reporter plasmid. Serum from early-PP controls (1-3 days after delivery) induced high NF-kB activation while serum from late-PP controls (2 weeks—10 months after delivery) displayed low NF-kB activation properties (FIG. 3A). Serum probes from PPCM patients were obtained 2 weeks up to 8 months after delivery and compared to late-PP women. As shown in FIG. 3B, serum of PPCM patients induced substantially more luciferase activity indicative for higher NF-kB activation compared to pregnancy matched postpartum controls. This activation was markedly blunted in RHE-A cells with siRNA-mediated down regulation of the uPAR (FIG. 3C), demonstrating that this stronger NF-kB activation by PPCM sera is mediated through the uPAR system. In order to analyze whether PAI-1 is responsible for this strong NF-kB activation by PPCM serum we incubated serum probes from two patients who had confirmed uPAR-dependent NF-kB activity with the PAI-1 inhibitor PAI-039 (Tiplaxtinin) prior addition to RHE-A cells. As shown in FIG. 3D, PAI-039 markedly blunted serum induced NF-kB activation in these PPCM serum probes.

Association of Gene Polymorphism in the PAI-1 Promoter with PPCM

Genetic aberrations such as genetic PAI-1 polymorphisms can lead to increased PAI-1 levels (Gils, 2004, Curr Med Chem 11:2323-2334). Specifically polymorphisms within the promoter region have been described which include a 4G/5G polymorphism at position −675 and a base substitution of A to G at position −844 (A-844-G) which appear to influence the gene expression level and may lead to a higher risk of thrombotic complications such as stroke and myocardial infarction, respectively miscarriages (Chen, 2015, Am J Reprod Immunol 73:292-300; Declerck, 2013, Semin Thromb Hemost 39:356-364). However, the incidence of these two gene polymorphisms was not higher in PPCM patients compared to healthy postpartum controls (FIGS. 4A and B).

Next, we cloned and sequenced the PAI-1 promoter from 3 PPCM patients who displayed high PAI-1 plasma levels and from 3 healthy postpartum controls. In one PPCM patient an additional polymorphism (substitution of C to T) was found at position −747 of the PAI-1 promoter (FIG. 4C). The patient was heterozygous for this polymorphism and homozygous for 4G/4G at position −675 and homozygous for A/A at position −844. This patient had high PAI-1 plasma levels at diagnosis of her index PPCM (i.e. the PPCM of her first pregnancy). At the beginning of her subsequent pregnancy, PAI-1 levels decreased and cardiac function increased until the third trimester. Thereafter, PAI-1 levels increased and remained high even after subsequent delivery, which was paralleled by a subtle decrease in cardiac function (FIG. 4D).

Discussion

We observed that PPCM patients display higher blood levels of PAI-1 at the time of diagnosis and a specific activation of NF-kB via the uPAR receptor compared to healthy postpartum controls or compared to patients with heart failure due to DCM. In addition, in patients with a high risk for developing PPCM due to a PPCM in a previous pregnancy, postpartum PAI-1 levels were increased even prior onset of heart failure indicating that PAI-1 may serve as biomarker for risk assessment for the disease. Finally, our data even suggest that patients with other causes for peripartum heart failure than PPCM, i.e. underlying genetic forms of cardiomyopathies, do not display unregulated PAI-1, a feature that suggests for the first time a biomarker that may distinguish between "true" PPCM and preexisting heart disease.

As shown in previous studies, biomarkers specific for cardiac damage such as troponin or CK are frequently within normal range in PPCM patients (Haghikia, 2013, Basic Res Cardiol 108:366). In turn, NT-proBNP, a global stress marker for heart failure, is elevated in the majority of PPCM patients but is not specific for the disease (Haghikia, 2013, Basic Res Cardiol 108:366). Other biomarkers that are associated with pathologies in pregnancy, i.e. sFlt1, display a highly specific kinetics during and after pregnancy and seem therefore difficult to be standardized. In contrast, our analyses on the kinetics of PAI-1 in healthy peripartum women indicate that PAI-1 levels remain in the range of non-pregnant controls during pregnancy and raise only moderately immediately before delivery. After delivery they decline within a day to non-pregnant control levels where they remain stable. PAI-1 serum and plasma levels appear relatively stable with regard to pH variations and freezing procedures (Hamon, 1990, Blood Coagul Fibrinolysis 1:393-399). Since commercial ELISA to measure plasma and serum PAI-1 (for example from R&D systems) are reliable and certified, PAI-1 emerges as the first PPCM specific biomarker that is easy to be measured and may even allow to distinguish PPCM from other forms of peripartum heart failure. Moreover, PAI-1 may serve as a biomarker for risk assessment in women that are considered to have a higher risk to develop PPCM.

In order to diagnose PPCM it is preferred not only to monitor PAI-1 serum and plasma levels in PPCM patients but also the specific activity of the PAI-1/16K prolactin, tPA/uPA/uPAR complex and its ability to activate NF-kB. In our study we developed a cell-based assay using RHE-A cells stably transfected with an NF-kB driven luciferase reporter plasmid to monitor the ability of PPCM serum to activate NF-kB. Indeed, we observed that serum from patients with acute PPCM display increased NF-kB activity compared to postpartum controls. Since NF-kB is a common pathway that is activated by many stress factors it is important to test if NF-kB activation derives from the PAI-1/16K prolactin, tPA/uPA/uPAR complex. In fact, we observed that NF-kB activation is increased in healthy postpartum women immediately after delivery together with increased levels of CRP while later after delivery NF-kB activation is not elevated anymore. Therefore, the NF-kB activity test is less suitable for PPCM patients at the time of delivery and is preferably used past one week after delivery. In addition, since other receptor systems may also activate NF-kB, the NF-kB activation through the uPAR complex has to be confirmed for example by using a cell-based assay lacking uPAR expression for comparison. Blocking PAI-1 directly with small molecule inhibitors such as PAI-039 (Fang, 2012, J Natl Cancer Inst 104:1470-1484) or other compounds (Placencio, 2015, PLoS One 10:e0133786) is another possibility to perform this test. In addition, our cell-based test system can also be used for pre-clinical screening for small molecules that block PAI-1/16K prolactin, tPA/uPA/uPAR-mediated NF-kB activation. Indeed, PAI-1 has been established as a therapeutic target in cancer and in thrombotic complications and several small molecule inhibitors have been designed to specifically inhibit PAI-1 such as PAI-039 (Fang, 2012, J Natl Cancer Inst 104:1470-1484) and other compounds (Placencio, 2015, PLoS One 10:e0133786). Here we present first evidences that pharmacological inhibition of PAI-1 in serum probes from PPCM patients reduced NF-kB activation in endothelial cells in vitro. These observations suggest that targeting PAI-1 and or NF-kB activation may offer novel therapeutic options to treat PPCM in patients or to prevent onset of PPCM in patients at risk for the disease.

It has been reported that gene polymorphisms in PAI-1 affect its expression and activity (Gils, 2004, Curr Med Chem 11:2323-2334; Chen, 2015, Am J Reprod Immunol 73:292-300; Declerck, 2013, Semin Thromb Hemost 39:356-364). Especially two polymorphisms in the promoter region of PAI-1, the 4G/5G polymorphism at position −675 and a base substitution of A to G at position −844 (A-844-G) seem to be associated with a higher PAI-1 expression and higher risk of thrombotic complications such as stroke and myocardial infarction, respectively miscarriages (Chen, 2015, Am J Reprod Immunol 73:292-300; Declerck, 2013, Semin Thromb Hemost 39:356-364). Although both polymorphisms are present in our PPCM patient collective, their frequency is similar in healthy postpartum controls suggesting that they seem not specifically prevalent in PPCM patients. In preliminary analyses we detected an additional polymorphism in the promoter region of one PPCM patient who displayed high PAI-1 levels at her index PPCM and also after her subsequent pregnancy. Thus, polymorphisms in PAI-1 and potentially also the uPAR may be novel risk factors for PPCM.

In conclusion, PAI-1 emerges as the first PPCM specific biomarker that is easy to be measured as a first screen either to detect a risk for PPCM or to diagnose the disease. Measurement of PAI-mediated NF-kB activity is a possibility to further diagnose the presence of PPCM causing pathomechanisms, which is important for treatment concepts that involve Bromocriptine and ablactation. Finally, targeting PAI-1 and/or NF-kB activation may be novel and highly efficient therapeutic concepts for prevention or treatment of PPCM.

TABLE 1

Summary of clinical data from PPCM and DCM patients and postpartum controls

| Parameters | PPCM Patients (n = 45) | Postpartum controls (n = 27) | DCM (n = 15) |
| --- | --- | --- | --- |
| Age (years, mean ± SD) | 36 ± 5 | 28 ± 5 | |
| Gravida: Median (range) | 2 (1-5) | 1 (1-3) | |
| Parity: Median (range) | 1 (1-4) | 1 (1-2) | |
| NYHA: Median (range) | 4 (2-4) | | |
| LVEF (%, mean ± SD) | 25 ± 9 | 68 ± 5 | 32 ± 9 |
| Heart rate (bpm, mean ± SD) | 91 ± 21 | | |
| Systolic BP (mmHg, mean ± SD) | 110 ± 18 | | |
| Diastolic BP (mmHg, mean ± SD) | 71 ± 13 | | |
| CRP (mg/l) Median (range) | 19 (1-161) | 33 (10-164) | |
| hsTnT (pg/ml) Median (range) | 14 (1-631) | 2 (2-5, 6) | |
| NT-proBNP (pmol/ml) Median (range) | 4382 (511-19723) | 57 (30-477) | 547 (71-2365) |

New York Heart Association (NYHA), left ventricular ejection fraction (LVEF), blood pressure (BP), C-reactive protein (CRP), high sensitive troponin T (hsTNT), N-terminal pro-Brain natriuretic peptide (NT-proBNP).

The present invention refers to the following nucleotide and amino acid sequences:

SEQ ID NO: 1: Nucleotide sequence of the mRNA of PAI-1

[Homo sapiens serpin peptidase inhibitor, clade E (nexin, plasminogen activator inhibitor type 1), member 1 (SERPINE1)]

SEQ ID NO: 2: Amino acid sequence of PAI-1

[Homo sapiens serpin peptidase inhibitor, clade E (nexin, plasminogen activator inhibitor type 1), member 1 (SERPINE1)]

SEQ ID NO: 3: Nucleotide sequence of the PAI-1 gene

[Homo sapiens serpin peptidase inhibitor, clade E (nexin, plasminogen activator inhibitor type 1), member 1 (SERPINE1), RefSeqGene on chromosome 7]

The invention claimed is:

1. A method for detecting plasminogen activator inhibitor-1 in a sample obtained from a test subject who has peripartum cardiomyopathy or is at risk for developing peripartum cardiomyopathy, wherein the method comprises:
   (a) obtaining a biological sample from a test subject who has peripartum cardiomyopathy or is at risk for developing peripartum cardiomyopathy;
   (b) measuring in said sample an amount and/or activity of plasminogen activator inhibitor-1;
   (c) comparing said amount and/or activity of plasminogen activator inhibitor-1 from the sample with reference data corresponding to the amount and/or activity of plasminogen activator inhibitor-1 of at least one reference subject.

2. The method of claim 1, wherein the at least one reference subject has peripartum cardiomyopathy; and wherein an identical or similar amount and/or activity of plasminogen activator inhibitor-1 of the test subject as compared to the reference data indicates the presence of peripartum cardiomyopathy or a risk for developing peripartum cardiomyopathy.

3. The method of claim 1, wherein step (a) comprises analyzing the amount and/or activity of the plasminogen activator inhibitor-1 protein and/or analyzing the amount of the plasminogen activator inhibitor-1 RNA.

4. The method of claim 1, wherein said amount of plasminogen activator inhibitor-1 is analyzed by ELISA.

5. The method of claim 1, wherein an amount and/or activity of plasminogen activator inhibitor-1 of the test subject, which is at least 125% of the reference data, indicates the presence of peripartum cardiomyopathy or a risk for developing peripartum cardiomyopathy.

6. The method of claim 1, wherein the time point for obtaining the sample is:
   (a1) between 1 day and 7 months after delivery of a baby if the amount of plasminogen activator inhibitor-1 is analyzed; and/or
   (a2) between 2 weeks and 7 months after delivery of a baby if the activity of plasminogen activator inhibitor-1 is analyzed.

7. The method of claim 1, further comprising identifying whether said subject has at least one of the risk factors selected from overweight, smoking, twin pregnancy, pregnancy-induced or independent hypertensive disorder, the pregnancy was made by in vitro fertilization, high blood pressure, and receipt of chemotherapy before the pregnancy.

8. The method of claim 1, further comprising identifying whether said subject has at least one of the symptoms selected from orthopnea, dyspnea, pitting edema, cough, frequent night-time urination, excessive weight gain during the last month of pregnancy, palpitations, chest pain, depression, fatigue and physical weakness.

9. The method of claim 1, wherein said sample is blood, blood plasma, blood serum or urine.

10. The method of claim 1, wherein the method uses a binding molecule for identifying a subject which has peripartum cardiomyopathy or which has a risk for developing peripartum cardiomyopathy, wherein said binding molecule specifically binds to at least one of the molecules defined in (a) to (c):
    (a) the plasminogen activator inhibitor-1 protein;
    (b) a nucleic acid molecule encoding the plasminogen activator inhibitor-1 protein; or
    (c) the plasminogen activator inhibitor-1/16 kDa prolactin complex.

11. The method of claim 1, wherein the amount of said plasminogen activator inhibitor-1 is measured.

12. The method of claim 1, wherein the activity of said plasminogen activator inhibitor-1 is measured.

13. The method of claim 1, wherein said test subject has peripartum cardiomyopathy.

14. The method of claim 5, wherein said test subject has peripartum cardiomyopathy.

15. The method of claim 6, wherein said test subject has peripartum cardiomyopathy.

16. The method of claim 10, wherein said test subject has peripartum cardiomyopathy.

* * * * *

SEQUENCE LISTING

```
<160> NUMBER OF SEQ ID NOS: 13

<210> SEQ ID NO 1
<211> LENGTH: 3207
<212> TYPE: DNA
```

<213> ORGANISM: Homo sapiens
<220> FEATURE:
<223> OTHER INFORMATION: Homo sapiens serpin peptidase inhibitor, clade E (nexin, plasminogen activator inhibitor type 1), member 1 (SERPINE1)

<400> SEQUENCE: 1

```
ggcccacaga ggagcacagc tgtgtttggc tgcagggcca agagcgctgt caagaagacc      60
cacacgcccc cctccagcag ctgaattcct gcagctcagc agccgccgcc agagcaggac     120
gaaccgccaa tcgcaaggca cctctgagaa cttcaggatg cagatgtctc agccctcac     180
ctgcctagtc ctgggcctgg cccttgtctt tggtgaaggg tctgctgtgc accatccccc     240
atcctacgtg gcccacctgg cctcagactt cggggtgagg gtgtttcagc aggtggcgca     300
ggcctccaag gaccgcaacg tggttttctc accctatggg gtggcctcgg tgttggccat     360
gctccagctg acaacaggag agaaaccca gcagcagatt caagcagcta tgggattcaa     420
gattgatgac aagggcatgg cccccgccct ccggcatctg tacaaggagc tcatggggcc     480
atggaacaag gatgagatca gcaccacaga cgcgatcttc gtccagcggg atctgaagct     540
ggtccagggc ttcatgcccc acttcttcag gctgttccgg agcacggtca gcaagtgga     600
cttttcagag gtgagagag ccagattcat catcaatgac tgggtgaaga cacacacaaa     660
aggtatgatc agcaacttgc ttgggaaagg agccgtggac agctgacac ggctggtgct     720
ggtgaatgcc ctctacttca cggccagtga agactccc ttccccgact ccagcaccca     780
ccgccgcctc ttccacaaat cagacggcag cactgtctct gtgcccatga tggctcagac     840
caacaagttc aactatactg agttcaccac gcccgatggc cattactacg acatcctgga     900
actgccctac cacggggaca ccctcagcat gttcattgct gcccccttatg aaaaagaggt     960
gcctctctct gccctcacca acattctgag tgcccagctc atcagccact ggaaaggcaa    1020
catgaccagg ctgccccgcc tctggttct gcccaagttc tccctggaga ctgaagtcga    1080
cctcaggaag cccctagaga acctgggaat gaccgacatg ttcagacagt ttcaggctga    1140
cttcacgagt cttttcagacc aagagcctct ccacgtcgcg caggcgctgc agaaagtgaa    1200
gatcgaggtg aacgagagtg gcacggtggc ctcctcatcc acagctgtca tagtctcagc    1260
ccgcatggcc cccgaggaga tcatcatgga cagaccctc ctctttgtgg tccggcacaa    1320
cccccacagga acagtccttt tcatgggcca agtgatggaa ccctgaccct ggggaaagac    1380
gccttcatct gggacaaaac tggagatgca tcgggaaaga agaaactccg aagaaaagaa    1440
ttttagtgtt aatgactctt tctgaaggaa gagaagacat ttgcctttg ttaaaagatg    1500
gtaaaccaga tctgtctcca agaccttggc ctctccttgg aggaccttta ggtcaaactc    1560
cctagtctcc acctgagacc ctgggagaga agtttgaagc acaactccct taaggtctcc    1620
aaaccagacg gtgacgcctg cgggaccatc tggggcacct gcttccaccc gtctctctgc    1680
ccactcgggt ctgcagacct ggttcccact gaggcccttt gcaggatgga actacggggc    1740
ttacaggagc ttttgtgtgc ctggtagaaa ctatttctgt tccagtcaca ttgccatcac    1800
tcttgtactg cctgccaccg cggaggaggc tggtgacagg ccaaaggcca gtggaagaaa    1860
caccctttca tctcagagtc cactgtgca ctggccaccc ctccccagta cagggtgct    1920
gcaggtggca gagtgaatgt cccccatcat gtggcccaac tcctctggcc tggccatctc    1980
cctcccagaa acagtgtgc atgggttatt ttggagtgta ggtgacttgt ttactcattg    2040
aagcagattt ctgcttcctt ttatttttat aggaatagag gaagaaatgt cagatgcgtg    2100
cccagctctt caccccccaa tctcttggtg ggaggggtg tacctaaata tttatcatat    2160
```

```
ccttgccctt gagtgcttgt tagagagaaa gagaactact aaggaaaata atattattta    2220
aactcgctcc tagtgtttct ttgtggtctg tgtcaccgta tctcaggaag tccagccact    2280
tgactggcac acacccctcc ggacatccag cgtgacggag cccacactgc caccttgtgg    2340
ccgcctgaga ccctcgcgcc ccccgcgccc ctcttttttcc ccttgatgga aattgaccat    2400
acaatttcat cctccttcag gggatcaaaa ggacggagtg gggggacaga gactcagatg    2460
aggacagagt ggtttccaat gtgttcaata gatttaggag cagaaatgca aggggctgca    2520
tgacctacca ggacagaact ttccccaatt acagggtgac tcacagccgc attggtgact    2580
cacttcaatg tgtcatttcc ggctgctgtg tgtgagcagt ggcacgtga ggggggggtg     2640 ggtgagagag acaggcagct cggattcaac taccttagat aatatttctg aaaacctacc    2700
agccagaggg tagggcacaa agatggatgt aatgcacttt ggggaggccaa ggcgggagga   2760 ttgcttgagc ccaggagttc aagaccagcc tgggcaacat accaagaccc ccgtctcttt    2820
aaaaatatat atattttaaa tatacttaaa tatatatttc taatatcttt aaatatatat    2880
atatatttta aagaccaatt tatgggagaa ttgcacacag atgtgaaatg aatgtaatct    2940
aatagaagcc taatcagccc accatgttct ccactgaaaa atcctctttc tttggggttt    3000
ttctttcttt cttttttgat tttgcactgg acggtgacgt cagccatgta caggatccac    3060
aggggtggtg tcaaatgcta ttgaaattgt gttgaattgt atgcttttc acttttgata     3120 aataaacatg taaaaatgtt tcaaaaaaat aataaaataa ataaatacga agaatatgtc    3180
aggacagtca aaaaaaaaaa aaaaaaa                                        3207
```

<210> SEQ ID NO 2
<211> LENGTH: 402
<212> TYPE: PRT
<213> ORGANISM: Homo sapiens
<220> FEATURE:
<223> OTHER INFORMATION: Homo sapiens serpin peptidase inhibitor, clade
     E (nexin, plasminogen activator inhibitor type 1), member 1
     (SERPINE1)

<400> SEQUENCE: 2

```
Met Gln Met Ser Pro Ala Leu Thr Cys Leu Val Leu Gly Leu Ala Leu
1               5                   10                  15

Val Phe Gly Glu Gly Ser Ala Val His His Pro Ser Tyr Val Ala
            20                  25                  30

His Leu Ala Ser Asp Phe Gly Val Arg Val Phe Gln Gln Val Ala Gln
        35                  40                  45

Ala Ser Lys Asp Arg Asn Val Val Phe Ser Pro Tyr Gly Val Ala Ser
    50                  55                  60

Val Leu Ala Met Leu Gln Leu Thr Thr Gly Gly Glu Thr Gln Gln Gln
65                  70                  75                  80

Ile Gln Ala Ala Met Gly Phe Lys Ile Asp Asp Lys Gly Met Ala Pro
                85                  90                  95

Ala Leu Arg His Leu Tyr Lys Glu Leu Met Gly Pro Trp Asn Lys Asp
            100                 105                 110

Glu Ile Ser Thr Thr Asp Ala Ile Phe Val Gln Arg Asp Leu Lys Leu
        115                 120                 125

Val Gln Gly Phe Met Pro His Phe Phe Arg Leu Phe Arg Ser Thr Val
    130                 135                 140

Lys Gln Val Asp Phe Ser Glu Val Glu Arg Ala Arg Phe Ile Ile Asn
145                 150                 155                 160
```

```
Asp Trp Val Lys Thr His Thr Lys Gly Met Ile Ser Asn Leu Leu Gly
            165                 170                 175

Lys Gly Ala Val Asp Gln Leu Thr Arg Leu Val Leu Val Asn Ala Leu
        180                 185                 190

Tyr Phe Asn Gly Gln Trp Lys Thr Pro Phe Pro Asp Ser Ser Thr His
    195                 200                 205

Arg Arg Leu Phe His Lys Ser Asp Gly Ser Thr Val Ser Val Pro Met
210                 215                 220

Met Ala Gln Thr Asn Lys Phe Asn Tyr Thr Glu Phe Thr Thr Pro Asp
225                 230                 235                 240

Gly His Tyr Tyr Asp Ile Leu Glu Leu Pro Tyr His Gly Asp Thr Leu
                245                 250                 255

Ser Met Phe Ile Ala Ala Pro Tyr Glu Lys Glu Val Pro Leu Ser Ala
            260                 265                 270

Leu Thr Asn Ile Leu Ser Ala Gln Leu Ile Ser His Trp Lys Gly Asn
        275                 280                 285

Met Thr Arg Leu Pro Arg Leu Leu Val Leu Pro Lys Phe Ser Leu Glu
    290                 295                 300

Thr Glu Val Asp Leu Arg Lys Pro Leu Glu Asn Leu Gly Met Thr Asp
305                 310                 315                 320

Met Phe Arg Gln Phe Gln Ala Asp Phe Thr Ser Leu Ser Asp Gln Glu
                325                 330                 335

Pro Leu His Val Ala Gln Ala Leu Gln Lys Val Lys Ile Glu Val Asn
            340                 345                 350

Glu Ser Gly Thr Val Ala Ser Ser Ser Thr Ala Val Ile Val Ser Ala
        355                 360                 365

Arg Met Ala Pro Glu Glu Ile Ile Met Asp Arg Pro Phe Leu Phe Val
    370                 375                 380

Val Arg His Asn Pro Thr Gly Thr Val Leu Phe Met Gly Gln Val Met
385                 390                 395                 400

Glu Pro

<210> SEQ ID NO 3
<211> LENGTH: 12178
<212> TYPE: DNA
<213> ORGANISM: Homo sapiens
<220> FEATURE:
<223> OTHER INFORMATION: Homo sapiens serpin peptidase inhibitor, clade
      E (nexin, plasminogen activator inhibitor type 1), member 1
      (SERPINE1)

<400> SEQUENCE: 3 gcccacaga ggagcacagc tgtgtttggc tgcagggcca agagcgctgt caagaagacc      60
cacacgcccc cctccagcag ctgaattcct gcagctcagc agccgccgcc agagcaggac    120
gaaccgccaa tcgcaaggca cctctgagaa cttcaggtag gagaaaagca aactccctcc    180
aacctcttac ttcgggctta aggcagagaa ctcgcctccc cagaatctcc tccctccatg    240 atccccccgct attcctctat tttcttttcc tcggacctgc agccttgggt cgaccctgcc    300
ctaggggtga ctgcaggaga gcagggagga tggtcaggcg tcaccaacaa ccccatcacc    360
cagtaacaag aaccttgact ctctcagtcc tctgcatca agacacttac ccatttccca     420
cctcatgcct gctaacttga atgaaacaat cgctgggaaa gcattaagag aattaaggct    480
gggcactgtg gctcatgcct gtaatcccag cactttgtga ggctgaggca ggcagataac    540
ttgagcccag gagtttgaga ccagcctggg caacatggca aaaccctgct ctcccaaaaa    600
```

-continued

```
aatacaaaaa ttagctgggc gtgctggtgt gcctgtattc ccagctactt gggaggctga    660
ggtgggagga ttgcttcagc tggggaggcg gaggctgcag ggagccaaga ctgagccatt    720
gcacccagcc tgggtgacag agcaagaccc tgtctctaaa aatgaatgaa aggaaggaag    780
aaagagagag aaagagagag aggaaagaag gaaggaagta aagaagaaag aaagaaagaa    840
agaggaaaga ggaagaaaga aagaaaagaa agaaagaaaa gaaagcaaa tttaaagctt     900 atgcaaatca aagatgttgt gataattgat aattgagtct gggctaaatt ccccctgggc    960
tgcaaaggca gagagtggta atgacttctc acctgctttt cttctaaggc tttttttacgg  1020 gacacagagg gaagggagat ggactggatt ccaagattcc cacagggcaa gatgggcgaa   1080
gactccctgc cactgcccgg ggataagtca gtctgagtga gacggagtgg gatgggctta   1140
gaacctgaac atgtcatggt ctcttcctgc accttgccct agtgttcact taccacctgc    1200
ttgcaggaaa caagaagagc agggcccaca gctggccagc tcccctcccc tcccgcctgt    1260
cttccagaac gattccttca ccagccctct ttccattgct ctaggatgca gatgtctcca    1320
gccctcacct gcctagtcct gggcctggcc cttgtctttg gtgaagggtc tgctgtgcac    1380
catcccccat cctacgtggc ccacctggcc tcagacttcg gggtgagggt gtttcagcag    1440
gtggcgcagg cctccaagga ccgcaacgtg gtttctcac cctatggggt ggcctcggtg     1500
ttggccatgc tccagctgac aacaggagga gaaacccagc agcagattca agcagctatg    1560
ggattcaaga ttgatggtga gccacgggac accaggggag gtgggtggca tgcagaacag   1620
acctaccaga agccaaggaa aggctggctc tggcttagcc gagccaagcc ccatacagct    1680
gtgctgcagg ggccacccca tcttcttccc actacactcc aagtcactgg acccttgaat    1740
ctccaagggt gtctgaccag tagatttacc gcttattcac caccgtgtga tcttaacctc   1800
gttaagtttg cccatctaca aaatgaggat tatttgctgt cctaaagaat tcatgagccg    1860
ggcgcggtgg ctcaaacgcc tgtaatccca gcactttggg aggccaaggc gggcggatca    1920
tgaggtcagg agatcaagac catcctggct aacacagtga aactccatct ctactaaaaa    1980
tacaaaaaaa attagccagg cgtggtggca ggcgcctgta gtcccagcta ctcgggaggc    2040
tgaggcagga gaatggcatg aacccaggag gcagagcttg cagtgagctg agatcgtgcc    2100
actgcactcc agcctgggcg acagagagag actccgtctc aaaaaaaaaa aataaaagaa    2160
ttcatggaat tacacttgtg aaatacttag catagccatc actataggaa aaaaatctaa    2220
ggccaggcac agtgcctcat gcctgtaatc tcagcacttt cggagtttga ggcaggagga    2280
tcacccaagg ctaggagttc aaggccagcc tgggcaatac ggtgaaaccc cgtctctaat    2340
aaaaatataa aaattagtct gatgaggtgg tgcacctgta atcccagcta ctcaggaagc    2400
tgagacacaa gaatcacttt aacccgggag gtggaggtgg cagtgagctg agatcacacc    2460
attgcactcc agcctgggtg acagagtgag acctgtcaaa aaaagaaaa gaaagagaga    2520 gagagagaga agagagagaa agaaagaaga gaaagaaag aaagagagag agaaagaa    2580 agaaagaaac aaagaaacaa agaaagaaag gaaagaaaa aaaaactaa ggccaggcaa    2640 ggtggcttat gactgtaatt tcagcacttt ggaagattga ggcaggagga tcacttgagg    2700
ccagaagttc gagacaagac tgagcaacag ggagacccct gcctctacaa aaaaatttac    2760
aaattagcca gatgtggtga cacatacctg tagtcccaac tactcaggag gctgaggtgg    2820
gaggatggct tgagcccagg agctggaggc tgcagtgagc tatgattgta ccactgcact    2880
tcagcctggg caacaagggg aagccctgtc tgaaaaaaaa aaaaaagaa aaagaagaag    2940 aaagaaaata tttagggttc atccaggagg cagaggttgc agtaagctga catcgcgcca    3000
```

```
ttgcactcca gcctgggaga caagagcaaa actccaactc aaaaaaaaaa aaaaaaaaaa    3060
aacaggaaga aaatatttag ggttcataat ttaagaacag agaaaaatat tctagcccaa    3120
agaaagggtt gggatctgag acttttgaag aaaggaagga gatacagaaa agagatttca    3180
tcctggaatg aaatctccct ccagagagcc ctggaaagc acggtagccc catccatca      3240 gagtggagcc ccttgtgggg gaagtgggct cggctgggaa ccctcaattc agcataagcc    3300
tcacatgtcc tctcctctct gtcccggtgc agacaagggc atggccccg ccctccggca     3360 tctgtacaag gagctcatgg ggccatggaa caaggatgag atcagcacca cagacgcgat    3420
cttcgtccag cgggatctga agctggtcca gggcttcatg ccccacttct tcaggctgtt    3480
ccggagcacg gtcaagcaag tggactttc agaggtggag agagccagat tcatcatcaa     3540
tgactgggtg aagacacaca caaaaggtga gcaggcaggg aaaggaaacc catttcctgg    3600
gcctcaagag aaagggaatt tggaaataaa tccacatatc ccagttgggt gcagtagttc    3660
acacctgtaa tcccagccca cactttggg aggtctaggc gagaggaagg cttgaggcct     3720
ggagtttgag accagcctgg ccaacataac aagacctcat ctcttcaaaa aatttaaaaa    3780
ccagccgggc atggtggtgc acacctgtag tcccagctac ttgggaggct gaggtgggag    3840
gatcacttga gtccagcagt tcaaggctgc agtgagctat gtttgcacca ccacactcca    3900
gcctgggtca cagaacaaga cctcatctct aaaaacaaa caaaaccaa atccacatat       3960 cctaaaaaat gctccttttc agcattctct tctctatgga caaagggctg gatgctttaa    4020
gaaccaaatc ttaggctggg cacggtggct cacgcctcta atcctagcac tttgagaggc    4080
caaggcgggc agattgcctg agcacaggag ttcgagacca gcctggccaa catggtgaaa    4140
ccctgtctct gtcaaaaata caaaaaatta gccaggtgtg ttggcgcatg cctataatcc    4200
cagctgctcg ggaggatgag gttcaaagaa tcacttgaac ccgggaggca gaggctgcag    4260
tgagctgaga tcatgccact gcactccagc ctgggtgaca gagcaagact ttgtctccaa    4320
aaaaaggaac tagacgggtt catttaaacc cctgactgca gcccttttgac atacatccaa   4380 ttgaggactg gggactccgg gaaacatcta aaaggcttaa aaactttgtc taacttcagc    4440
cgggcatggt ggctcacacc tgtaatccca gcactttggg aggctaaggc aggtggatca    4500
aaaggtcagg agtttgagac gagcctgacc aacatggtga acccccgtct ctactaaaaa    4560
tacaaaaatt agccaggcat ggtggcaggc gcctgtaatc ccagctattc gggaggctga    4620
ggcaggagaa ttgcttgaac cccggagaca gaggttgcag cgagccgaga tcgcgccact    4680
gcactccagc ctggcaatag agtgagactc catctcaaaa caacaacaac aacaacaaca    4740
aaatcgtcta acttcctgat cttcctgatc attgattttc ccataggtat gatcagcaac    4800
ttgcttggga aaggagccgt ggaccagctg acacggctgg tgctggtgaa tgccctctac    4860
ttcaacggcc agtggaagac tcccttcccc gactccagca cccaccgccg cctcttccac    4920
aaatcagacg gcagcactgt ctctgtgccc atgatggctc agaccaacaa gttcaactat    4980
agtaagtcca agagcccctt ccccacagcc cacagcaact gcatctcatt cctggggtct    5040
cccaaggaat acccaaaatg tcaccctctg agggaggaag accacaggga atgctcccct    5100
ttaagggagg agagaccccta gaatatactc cagctttgac aaagatttcc caagcaggag   5160
acatcaggat aatgggaaca gaagacagga ggtttatccc atgaaggatg aagaagctga    5220
aatccagaga ttccctcagg gccacatttg tccacctgac tccagggtct catcttcgtg    5280
tgttgctagt gtgattacct ggggatgaga aatcctgctg ggggagttga ggttaagagg    5340
```

```
atgaggactc caggtgctgt ggctcacgcc tgtaatccca gcactttggg aggccaaggc    5400
aggtggatca ggagtttgag gtcaggagtt tgagaccagc ctggccaaca tggtgaaacc    5460
ctgtctctac taaaaatgca aaaattagcc aggtgtggtg gcaggcgcct gtaatcccag    5520
ctactcggga ggctgaggca ggagaatcac ttgagcccgg gaggtggagg ttgcagtgag    5580
ccgaacgaaa ttgagccact tcacccccagc ctgggcaaaa gagtgaaatt ccattcaaaa    5640
aaaaaaaaaa aaaaaaaagg atgaggactg ggatgaactg gtggctgggt gtggggaaaa    5700
tggaagtgaa ggaaggccaa agagacaga gaaggcctgg cgcggcgact cacgcctata    5760
atcccagcac tttgggaggc tgagaagggg gattgcttga ggccagaagt tgaataccag    5820
tctgggcagc atagcaagac cctgcctcta caaaaaaaaa attttttta attagccagg    5880
cttggtgaca tgcatctgta gtctactcaa gaagctgagg tgaggccagg cacggtggct    5940
cacgcctgta ttcccagcac tttgggaggt caaggcgggt ggatgacctg aggtcaggag    6000
ttcaagacca gcctggccaa catggtgaaa ccccatctgt ataaaaatac aaaaattagc    6060
tgggcatgat agcaggtgcc tgtaattcca gctactcagg aggctgaggt gggagaatct    6120
attgaacccg ggagggggag gttgcagtga gccgagatca tgccattgca ctccagcctg    6180
ggcgacagag tgagactcct tctcaaaaca aacaaacaaa caaacaaaca aaatacagaa    6240
gctgaggcgg gaggaacatt tgaaccggat tcggaggctg cagtgagcta tgattgcacc    6300
actgcgctcc agtctgtgtg acagtgagac cctgtctctt acacacacac acacacacac    6360
acacatgcac acacacagag agagagaaat tagaagatac tgaattggca gaagagaagg    6420
gaaatagaaa ttaaaatact gaataggga gcagtgaaca ggggatacc aaaagccaag    6480
agcgagagag agcctggctt ccagaaatag tggagaagcc aggagaacta ggtgaaaacc    6540
cagtgctggg ttgccatcag cgagagctgg agccatttcc aacgaaccat cttgtcgtct    6600
tcacagctga gttcaccacg cccgatggcc attactacga catcctggaa ctgccctacc    6660
acggggacac cctcagcatg ttcattgctg ccccttatga aaaagaggtg cctctctctg    6720
ccctcaccaa cattctgagt gcccagctca tcagccactg gaaaggcaac atgaccaggc    6780
tgccccgcct cctggttctg cccaagtaag ccaccccgct atctccccga cctaccaacc    6840
cctctctcct ggctccctaa agtcaccgcc cccaggttga atttcccaga tctgtgatgc    6900
ttgcaggaca tgcatgtgtg ggaggctgat gggaaactgt ggcctgggtt tgattatgag    6960
tcttgcaatc atccctcccc ctgtttctgc tggagggcag gggacagctc ttcctgacca    7020
caccccaca ttgactatcc ccagaatacc cagcaaaagc ccccaaaagg agagtcagag    7080
aaatgaggga ggtgggggcc caatcagtcc acatctactt agggtcgccc catcagcact    7140
tccatcccca accctttcaa gtcaacatcc aaacaaaaga aatcacttcc aaggacggag    7200
cagctcaaag cgcagcttct agctgggtt ccaagaaagc agattttcg aaatccttct    7260
gcagaaggaa gcaaagagat tttttgaaat ctttctgcag aaggagaagg ctggagctgg    7320
ggaactccag aattataggg aagcctccca ccacgctcat cccaaatttc cggatgctat    7380
aatgccaggc ttggggaaag aggagaattt agttggttag ctggtgcgtg ctctcacttg    7440
catcctctct cttcctcttt ttttttttc tcctctctct ctggctcata aaatgggagg    7500
taattagttg tgccctggtg agaagcagag agtgcacaaa ggcccctgc ttgagtcctc    7560
ttcagggtta gctctcagaa acacaatctg cagaacagat ttttgttcca acatccttgc    7620
aggagaattt gcccttagct tcccccaccc cagccaggct gaataaaatt atgctgaaac    7680
tactgtctta tttgaggaaa gtaattagtc ataggtggga gggggtgggg agattgcaga    7740
```

```
agaatgttca tgaatattag gattttcagc tctaagggg gactttgtaa acagctttag    7800
aagaagaacc aggccggctg ggtgtggtgg ctcatgcctg taatctcagc atttggggag    7860
gccaaggcgg gcggatcact tgaggtcagg agtttgagac cagcctggcc aacatggtga    7920
aaccctgtct ctattaaaaa tacaaaaatt agccagccgt ggtagcgagc gcctatgatc    7980
ccagctactc cggaggctga ggccagagaa tcacatgaac ctgggaggtg gaggctgcag    8040
tgagccgaga tcacgccact gcactccagc ctggggaca agcaagaat ctgtttcaaa    8100 aaaaaaaaaa gaaaatagg aaggaaggaa ggaaaggaaa ggaaagaaga gagagagaaa    8160
gaaagagaga gagagaaaga aagaaagaaa gaaagaaaga aagaaagaaa gaaagaaaga    8220
aagaaagaaa gaaagaaaaa gaaaggaaag aaagaacgaa cgaaccaggc ctccctctcc    8280
aaccttcacc tccgtcccta ttctggccac ttgattcggg ggacacctgg taggggatgg    8340
ggaaaggtgg gagctgccag ccagagggga ccccggcttg agcagcctct tgctgctatc    8400
tgcaggttct ccctggagac tgaagtcgac ctcaggaagc ccctagagaa cctgggaatg    8460
accgacatgt tcagacagtt tcaggctgac ttcacgagtc tttcaggtaa gaagactttc    8520
cttggcattt tctcacccca gtggactgcg ggggcccta agaggaaaaa ggaacctctc    8580
cttgagagcg gcagctgatc taatcctgta tccacatctg tttcagacca agagcctctc    8640
cacgtcgcgc aggcgctgca gaaagtgaag atcgaggtga acgagagtgg cacggtggcc    8700
tcctcatcca caggtgagtc tggctcaggt gaggctccac gggtgtcgcc tccatcgccc    8760
ttcaggataa ctggtcccca gacccggaaa ggaccccgca gccctctcgg cacagagcag    8820
ctctgtctgt gctcagccat cacccactcc ccacctgttt ctcagcctgg aaaacgggct    8880
tgggaccatg gaaccctgtt tcctcgcctg atggctccta agttccctga ctgtgaaaag    8940
gcctcctaaa gaaaaaccca agttgttccc acagtgggaa gtaaacttaa gaaacatgct    9000
tatcaggctg ggcatggtgg ctcccacctg taatcccagc gctttggggg accaaggcag    9060
gtggatcact tgaggtcagg aattcgagac cagcctgggc aacatggcaa acccctatct    9120
ctactaaaaa tacaaaaatt aggcaggcgt ggtggcatgt gcctgtagtc ccagctactt    9180
gggaggctga ggcaggagaa tcacttgaat ccaggaggca gaggttgcag tgagccgaga    9240
tcacgctgct gcactccagc ctgggcaata gagcatgact ctgaagaaaa gaaagaaaga    9300
aagagagaga gagagaaaag aaagaaagaa agaaagaaag aaagaaagaa agaaagaaag    9360
aaagaaagaa agaaagagaa agaaagagaa gaaagaaaa gaaagagctt atcaataagc    9420
ccttaaagga tttagataaa tgtgtgtaag ggaagagctg atccattgct accaagctcc    9480
tggaggaaac caggtctcag aggatgtccc taaacttta aggttcatat tcaggaaaac    9540
aaacaacttc cagctgggct tagtggctca cacctgtaat cccagcactt tgggaggccg    9600
aggcaggagg atcgcttgag cccaggaatt tgagaccagc ctgggcaata taatgagact    9660
gtgtctctac aaaaattaga aaaaattag ccaggcatgg tggcatgcac ctgtagcccc    9720
agttacttgg gagactgagg tgggaggatc acttgagccc atgagttcaa ggctgcagtg    9780
agccatgaag gtgccactgc actcccacct gggcgacaga gggagaccct gtctctaaga    9840
aaaacggcgg gggtgggggt ggtgccagtg ccagcatccc tctgttctaa gacattgtcc    9900
cttctcttgc agctgtcata gtctcagccc gcatggcccc cgaggagatc atcatggaca    9960
gacccttcct ctttgtggtc cggcacaacc ccacaggtga gcctggaacc catcacgttc    10020
cacatcctcc cacccattct ttctctcagg aactagtccc gacagatgca gacatccctc    10080
```

```
tatccctgag agggctctgg gcagggaacc cataaccta ccctgcttcc tgtcccaaga    10140
ggaggctacc ttctatcacc cacagacagt gccgggtccc cgctctgtga ctcaggcagc    10200
tgcgactcca gacagctcac tcatctgcct agatctcagt ccttccaccc acatccagcc    10260
tgatgagctg tcccactcct tctgcttctc aaccccatg gttcttccac cctcaggaac     10320
agtccttttc atgggccaag tgatggaacc ctgaccctgg ggaagacgc cttcatctgg     10380
gacaaaactg gagatgcatc gggaaagaag aaactccgaa gaaagaatt ttagtgttaa     10440
tgactctttc tgaaggaaga gaagacattt gccttttgtt aaaagatggt aaaccagatc    10500
tgtctccaag accttggcct ctccttggag gaccttagg tcaaactccc tagtctccac     10560
ctgagaccct gggagagaag tttgaagcac aactcccta aggtctccaa accagacggt     10620
gacgcctgcg ggaccatctg gggcacctgc ttccacccgt ctctctgccc actcgggtct    10680
gcagacctgg ttcccactga gggccctttgc aggatggaac tacggggctt acaggagctt   10740
ttgtgtgcct ggtagaaact atttctgttc cagtcacatt gccatcactc ttgtactgcc    10800
tgccaccgcg gaggaggctg gtgacaggcc aaaggccagt ggaagaaaca ccctttcatc    10860
tcagagtcca ctgtggcact ggccacccct ccccagtaca ggggtgctgc aggtggcaga    10920
gtgaatgtcc cccatcatgt ggcccaactc tcctggcctg gccatctccc tccccagaaa    10980
cagtgtgcat gggttatttt ggagtgtagg tgacttgttt actcattgaa gcagatttct    11040
gcttcctttt attttatag gaatagagga agaaatgtca gatgcgtgcc cagctcttca    11100
cccccccaatc tcttggtggg gaggggtgta cctaaatatt tatcatatcc ttgcccttga   11160
gtgcttgtta gagagaaaga gaactactaa ggaaaataat attatttaaa ctcgctccta    11220
gtgtttcttt gtggtctgtg tcaccgtatc tcaggaagtc cagccacttg actggcacac    11280
accctccgg acatccagcg tgacggagcc cacactgcca ccttgtggcc gcctgagacc    11340
ctcgcgcccc ccgcgcccct ctttttcccc ttgatggaaa ttgaccatac aatttcatcc    11400
tccttcaggg gatcaaaagg acggagtggg gggacagaga ctcagatgag gacagagtgg    11460
tttccaatgt gttcaataga tttaggagca gaaatgcaag gggctgcatg acctaccagg    11520
acagaacttt ccccaattac agggtgactc acagccgcat tggtgactca cttcaatgtg    11580
tcatttccgg ctgctgtgtg tgagcagtgg acacgtgagg ggggggtggg tgagagagac    11640
aggcagctcg gattcaacta ccttagataa tatttctgaa aacctaccag ccagagggta    11700
gggcacaaag atggatgtaa tgcactttgg gaggccaagg cgggaggatt gcttgagccc    11760
aggagttcaa gaccagcctg gcaacatac caagacccc gtctctttaa aaatatatat     11820
atttttaaata tacttaaata tatatttcta atatctttaa atatatatat atattttaaa   11880
gaccaattta tgggagaatt gcacacagat gtgaaatgaa tgtaatctaa tagaagccta    11940
atcagcccac catgttctcc actgaaaaat cctctttctt tggggttttt ctttctttct    12000
tttttgattt tgcactggac ggtgacgtca gccatgtaca ggatccacag gggtggtgtc    12060
aaatgctatt gaaattgtgt tgaattgtat gcttttcac ttttgataaa taaacatgta     12120
aaatgtttc aaaaaaataa taaaataaat aaatacgaag aatatgtcag gacagtca      12178
```

<210> SEQ ID NO 4
<211> LENGTH: 102
<212> TYPE: DNA
<213> ORGANISM: Artificial Sequence
<220> FEATURE:
<223> OTHER INFORMATION: PAI-1 promoter

<400> SEQUENCE: 4

```
ccagcacacc tccaacctca gccagacaag gttgttgaca caagagagcc ctcaggggca    60
cagagagagt ctggacacgt ggggagtcag ccgtgtatca tc                       102

<210> SEQ ID NO 5
<211> LENGTH: 102
<212> TYPE: DNA
<213> ORGANISM: Artificial Sequence
<220> FEATURE:
<223> OTHER INFORMATION: PAI-1 promoter 01-016 clone #1

<400> SEQUENCE: 5
ccagcacact tccaacctca gccagacaag gttgttgaca caagagagcc ctcaggggca    60
cagagagagt ctggacacgt ggggagtcag ccgtgtatca tc                       102

<210> SEQ ID NO 6
<211> LENGTH: 102
<212> TYPE: DNA
<213> ORGANISM: Artificial Sequence
<220> FEATURE:
<223> OTHER INFORMATION: PAI-1 promoter 01-016 clone #2

<400> SEQUENCE: 6
ccagcacacc tccaacctca gccagacaag gttgttgaca caagagagcc ctcaggggca    60
cagagagagt ctggacacgt ggggagtcag ccgtgtatca tc                       102

<210> SEQ ID NO 7
<211> LENGTH: 102
<212> TYPE: DNA
<213> ORGANISM: Artificial Sequence
<220> FEATURE:
<223> OTHER INFORMATION: PAI-1 promoter 01-016 clone #3

<400> SEQUENCE: 7
ccagcacacc tccaacctca gccagacaag gttgttgaca caagagagcc ctcaggggca    60
cagagagagt ctggacacgt ggggagtcag ccgtgtatca tc                       102

<210> SEQ ID NO 8
<211> LENGTH: 102
<212> TYPE: DNA
<213> ORGANISM: Artificial Sequence
<220> FEATURE:
<223> OTHER INFORMATION: PAI-1 promoter 01-016 clone #4

<400> SEQUENCE: 8
ccagcacact tccaacctca gccagacaag gttgttgaca caagagagcc ctcaggggca    60
cagagagagt ctggacacgt ggggagtcag ccgtgtatca tc                       102

<210> SEQ ID NO 9
<211> LENGTH: 102
<212> TYPE: DNA
<213> ORGANISM: Artificial Sequence
<220> FEATURE:
<223> OTHER INFORMATION: PAI-1 promoter 01-016 clone #5

<400> SEQUENCE: 9
ccagcacact tccaacctca gccagacaag gttgttgaca caagagagcc ctcaggggca    60
cagagagagt ctggacacgt ggggagtcag ccgtgtatca tc                       102

<210> SEQ ID NO 10
<211> LENGTH: 825
<212> TYPE: DNA
```

<213> ORGANISM: Artificial Sequence
<220> FEATURE:
<223> OTHER INFORMATION: PAI-1 Pomoter

<400> SEQUENCE: 10

```
aagcttttac catggtaacc cctggtcccg ttcagccacc accaccccac ccagcacacc      60
tccaacctca gccagacaag gttgttgaca caagagagcc ctcaggggca cagagagagt     120
ctggacacgt ggggagtcag ccgtgtatca tcggaggcgg ccgggcacat ggcagggatg     180
agggaaagac caagagtcct ctgttgggcc caagtcctag acagacaaaa cctagacaat     240
cacgtggctg gctgcatgcc ctgtggctgt tgggctgggc ccaggaggag ggaggggcgc     300
tctttcctgg aggtggtcca gagcaccggg tggacagccc tgggggaaaa cttccacgtt     360
ttgatggagg ttatctttga taactccaca gtgacctggt tcgccaaagg aaaagcaggc     420
aacgtgagct gttttttttt tctccaagct gaacactagg ggtcctaggc ttttgggtc      480
acccggcatg gcagacagtc aacctggcag gacatccggg agagacagac acaggcagag     540
ggcagaaagg tcaagggagg ttctcaggcc aaggctattg gggtttgctc aattgttcct     600
gaatgctctt acacacgtac acacacagag cagcacacac acacacacac acatgcctca     660
gcaagtccca gagagggagg tgtcgagggg gacccgctgg ctgttcagac ggactcccag     720
agccagtgag tgggtggggc tggaacatga gttcatctat ttcctgccca catctggtat     780
aaaaggaggc agtggcccac agaggagcac agctgtgttt ggctg              825
```

<210> SEQ ID NO 11
<211> LENGTH: 23
<212> TYPE: DNA
<213> ORGANISM: Artificial Sequence
<220> FEATURE:
<223> OTHER INFORMATION: forward primer

<400> SEQUENCE: 11

```
aagcttttac catggtaacc cct                                              23
```

<210> SEQ ID NO 12
<211> LENGTH: 21
<212> TYPE: DNA
<213> ORGANISM: Artificial Sequence
<220> FEATURE:
<223> OTHER INFORMATION: reverse primer

<400> SEQUENCE: 12

```
gcagccaaac acagctgtgc t                                                21
```

<210> SEQ ID NO 13
<211> LENGTH: 20
<212> TYPE: DNA
<213> ORGANISM: Artificial Sequence
<220> FEATURE:
<223> OTHER INFORMATION: T7 primer

<400> SEQUENCE: 13

```
taatacgact cactataggg                                                  20
```